United States Patent
Aomatsu

(10) Patent No.: US 7,309,719 B1
(45) Date of Patent: Dec. 18, 2007

(54) STABILIZED PHARMACEUTICAL PREPARATION OF GAMMA-AMINOBUTYRIC ACID DERIVATIVES AND PROCESS FOR PREPARING THE SAME

(75) Inventor: Akira Aomatsu, Hachioji (JP)

(73) Assignee: Warner Lambert Company, LLC, Morris Plains, NJ (US)

( * ) Notice: Subject to any disclaimer, the term of this patent is extended or adjusted under 35 U.S.C. 154(b) by 0 days.

(21) Appl. No.: 09/674,815

(22) PCT Filed: May 10, 1999

(86) PCT No.: PCT/US99/10190

§ 371 (c)(1), (2), (4) Date: Dec. 7, 2000

(87) PCT Pub. No.: WO99/59573

PCT Pub. Date: Nov. 25, 1999

(30) Foreign Application Priority Data

May 15, 1998 (JP) .................................. 10-133113

(51) Int. Cl.
*A61K 31/195* (2006.01)
*A61K 31/4709* (2006.01)
*A61K 9/52* (2006.01)

(52) U.S. Cl. ..................... 514/561; 514/312; 424/451
(58) Field of Classification Search ................ 514/561, 514/12; 424/451, 497
See application file for complete search history.

(56) References Cited

U.S. PATENT DOCUMENTS

| | | | |
|---|---|---|---|
| 4,024,175 A | 5/1977 | Satzinger et al. | 260/468 |
| 4,087,544 A | 5/1978 | Satzinger et al. | 424/305 |
| 4,126,684 A | 11/1978 | Robson et al. | 424/254 |
| 4,255,448 A * | 3/1981 | Fariello | 514/578 |
| 4,540,582 A * | 9/1985 | Seiler et al. | 514/561 |
| 4,595,697 A * | 6/1986 | Seiler et al. | 514/534 |
| 4,952,560 A | 8/1990 | Kigasawa et al. | 514/2 |
| 5,025,035 A | 6/1991 | Wallace | 514/530 |
| 5,084,479 A | 1/1992 | Woodruff | 514/530 |
| 5,248,678 A * | 9/1993 | Costa et al. | 514/220 |
| 5,260,337 A * | 11/1993 | Sims et al. | 514/570 |
| 5,510,381 A | 4/1996 | Pande | 514/561 |
| 5,563,175 A * | 10/1996 | Silverman et al. | 514/561 |
| 5,629,008 A * | 5/1997 | Lee | 424/426 |
| 5,660,861 A * | 8/1997 | Jao et al. | 424/465 |
| 5,792,451 A * | 8/1998 | Sarubbi et al. | 424/85.4 |
| 6,028,102 A * | 2/2000 | Bialer et al. | 514/489 |
| 6,054,482 A * | 4/2000 | Augart et al. | 514/561 |
| 6,172,041 B1 * | 1/2001 | McCabe et al. | 514/12 |
| 6,383,471 B1 * | 5/2002 | Chen et al. | 424/45 |
| 6,576,790 B1 * | 6/2003 | Tenconi et al. | 562/507 |
| 6,833,140 B2 * | 12/2004 | Cundy et al. | 424/468 |
| 6,979,462 B1 * | 12/2005 | Spireas | 424/451 |
| 7,056,951 B2 * | 6/2006 | Spireas | 514/561 |

FOREIGN PATENT DOCUMENTS

| | | |
|---|---|---|
| EP | 0 376 891 A1 | 12/1989 |
| EP | 0 458 751 A1 | 5/1991 |
| JP | 63 253022 A | 10/1988 |
| WO | WO 9611680 A2 * | 4/1996 |

OTHER PUBLICATIONS

Liu, et al., "Potentiation of gamma-vinyl GABA(vigabatrin) effects by glycine", 1990, Eur. J. Pharmacol., 182:109-115.*
Peterson, et al., "Potentiation by glycine of anticonvulsant drugs in maximal electroshock seizures in rats"., 1990, Neuropharmacology, 29:392-409.*
Seiler and Sarban, "Synergistic anticovulsant effects of a GABA agoinst and glycine", 1984, Gen. Pharmacol., 15:367-369.*
Toth and Laijtha, "Glycine potentiates the action of some anticonvulsant drugs in some seizure models", 1984, Neurochem. Res., 8:1711-1718.*
Wood, et al., "Amplification by glycine of the effect of the GABA transport inhibitor THPO on synaptosomal GABA level", 1988, Neurochem. Res., 13:917-921.*
("Theoretical Biology and Medical Modelling", BioMed Central, 3:15, Mar. 22, 2006.*

* cited by examiner

*Primary Examiner*—Brian Kwon
(74) *Attorney, Agent, or Firm*—Paul Misiak; Scott Williams; Austin Zhang

(57) ABSTRACT

The present invention provides a stabilized pharmaceutical preparation of a 4-amino-3-substituted-butanoic acid derivative which can be obtained by incorporating an amino acid as a stabilizer.

5 Claims, No Drawings

STABILIZED PHARMACEUTICAL PREPARATION OF GAMMA-AMINOBUTYRIC ACID DERIVATIVES AND PROCESS FOR PREPARING THE SAME

This application is a 371 of PCT/US99/10190 filed May 10, 1999 which claims a benefit of JAPAN 133113/98 filed May 15, 1998.

FIELD OF THE INVENTION

This invention relates to a stabilized solid or liquid pharmaceutical preparation comprising a 4-amino-3-substituted-butanoic acid derivative and a process for the preparation of the same.

Particularly, the invention is concerned with a stabilized solid or liquid pharmaceutical preparation of the 4-amino-3-substituted-butanoic acid derivative, including gabapentin, pregabalin, baclofen, 3-aminomethyl-4-cyclohexyl-butanoic acid, 3-aminomethyl-5-cyclohexyl pentanoic acid, 3-aminomethyl-4-phenyl-butanoic acid or 3-aminomethyl-5-phenyl-pentanoic acid and a process for the preparation of the same.

More particularly, the invention is concerned with a stabilized solid pharmaceutical preparation of a 4-amino-3-substituted-butanoic acid derivative, including gabapentin, pregabalin or baclofen, in the dosage forms of tablets, powders, granules and capsules and a stabilized liquid pharmaceutical preparation in the dosage forms of liquid preparations, syrups and injections, as well as a process for the preparation of the same.

BACKGROUND OF THE INVENTION 1-(Aminomethyl)cyclohexaneacetic acid, one of the 4-amino-3-substituted-butanoic acid derivatives, having the following structural formula is disclosed in U.S. Pat. Nos. 4,024,175 and 4,087,544 and has been called "gabapentin", a generic name, due to its structural relation to γ-aminobutyric acid (GABA).

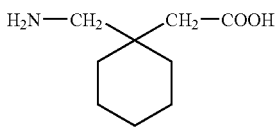

Gabapentin easily passes across the brain barrier. Owing to this, the compound is used as a medicine for the treatment of certain cerebral diseases such as certain forms of epilepsy, faint and hypokinesia as well as cranial traumas, and also for improving the cerebral functions in senile patients.

Moreover, U.S. Pat. No. 5,084,479 discloses that gabapentin is used for the treatment of neurodegenerative disorders such as Alzheimer's disease, Huntington's chorea or Parkinson's disease and amyotrophic lateral sclerosis. U.S. Pat. No. 5,025,035 discloses that gabapentin is used for the treatment of depression. U.S. Pat. No. 5,510,381 discloses that this compound is used for the treatment of mania and bipolar disorder. Furthermore, this compound, having an analgesic activity, is expected to be used as analgesics. Under these circumstances, there has been a greatly increased utility of gabapentin as the therapeutic agents for those diseases or disorders or conditions as recited above, in addition to cerebral diseases such as epilepsy and the like.

As stated above, gabapentin is a very effective drug for cerebral diseases such as epilepsy and the like, and it has an extremely low toxicity. However, in order to maintain the effect as expected, it has been administered to adults usually at a single daily dose of 900-1800 mg or in some cases a daily dose of up to 2400 mg in three divided doses. Thus, a single dose will be in the range of 300-600 mg or in some cases up to 800 mg.

Further, gabapentin has difficulties in that it is a drug having a strongly bitter taste and also a very poor fluidity and that an extremely high dosage should be required for administration in the dosage form of powders. Since gabapentin is very difficult to formulate because of its instability, gabapentin capsules now available in the oversea markets are those manufactured by a simple dry blending of gabapentin with necessary auxiliaries and subsequent encapsulating into hard capsules.

However, a single dose is as high as 300-600 mg or in some cases up to 800 mg as stated above, which necessitates large-sized capsules: for example, Capsule No. 0 should be applied to capsules having a content of 400 mg per capsule. Consequently, ingesting such capsules is difficult even for adults, much more for children. Although gabapentin capsules have already been marketed, it is still indispensable to attempt any improvement in compliance and easy administration of gabapentin, and a demand for a smaller-sized pharmaceutical preparation of gabapentin exists in the clinical field.

However, gabapentin in its aqueous solution shows a very poor stability so that autodegradation may be easily brought about. The mechanism of this autodegradation may be that the intramolecular condensation between the amino group and the carboxyl group within the gabapentin molecule is caused through a dehydration reaction to form 4-cyclohexylvinylpyrrolidone (the corresponding lactam form). In this regard, the autocondensation reaction rate may be variable depending upon storage temperature and can be far more accelerated as the temperature is elevated. Thus, this is the greatest reason why it has been difficult to manufacture a liquid pharmaceutical preparation of gabapentin.

On the other hand, another reason for difficulty in manufacturing a pharmaceutical preparation of gabapentin lies in that gabapentin itself is a powdery material having very poor compression-moldability and fluidity. Compression molding or granulation has been usually employed for small-sizing or fluidizing drugs which have such powder properties, and these molding properties should be improved with the aid of pharmaceutical auxiliaries. However, many of the auxiliaries to be applied for the purposes will accelerate the dehydration reaction between the amino group and the carboxyl group within the molecule of gabapentin to produce the corresponding lactam form, as the intramolecular condensation of gabapentin in its aqueous solution is accelerated. This dehydration reaction would be far more accelerated as the gabapentin powder is being more tightly compressed. Moreover, the reaction between gabapentin and such auxiliaries with lapse of time would be further accelerated by the use of water or an organic solvent in manufacturing a pharmaceutical preparation.

In short, it has been elucidated that the degradation of gabapentin with lapse of time due to the formation of the lactam is the phenomenon which shall be ascribed to the chemical structure of gabapentin itself and developed by the influence of water, irrespective of whether or not gabapentin is in the state of a solution or a solid.

It has been standardized in commercially available gabapentin capsules that an allowable content of the lactam up to the beyond-use date may be no more than 1.0% in view of safety. Accordingly, it is necessary in manufacturing a pharmaceutical preparation of gabapentin to prevent the formation of the lactam by retarding the dehydration reaction between the amino group and the carboxyl group within the molecule of gabapentin. On the other hand, it is a great problem to develop an adequate dosage form for easier ingesting, as discussed above.

Thus, in order to prepare a liquid pharmaceutical preparation of gabapentin, there have been made studies on, for example, controlling of pH, controlling of activity of water. Also, there have been attempted various methods, in order to form a smaller-sized solid pharmaceutical preparation of gabapentin. However, all of these prior art methods to manufacture solid or liquid preparations of gabapentin have not yet succeeded due to the presence of the lactam form found as the results of stability tests. Because of this, a pharmaceutical preparation of gabapentin now commercially available is limited to large-sized hard capsules only, although there has been a continuous need from the clinical field.

Such instability as encountered in manufacturing a gabapentin preparation has been also observed in other 4-amino-3-substituted-butanoic acid derivatives which are structurally analogous to gabapentin and have a structurally bulky substituent at the 3-position thereof similarly to gabapentin.

For example, 4-amino-3-p-chlorophenyl)butanoic acid, which is represented by the following structural formula and called "baclofen" in a generic name.

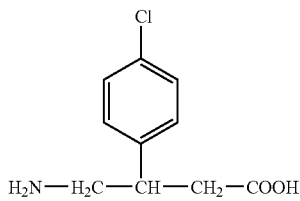

and 5-methyl-3-aminomethyl-hexanoic acid, which is represented by the following structural formula and called "pregabalin" in a generic name,

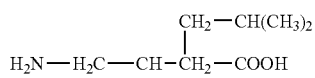

are also a drug which has very poor compression-moldability and fluidity like gabapentin. Compression molding or granulation used for small-sizing or fluidizing the drug should be improved with the aid of pharmaceutical auxiliaries. However, many of the auxiliaries to be applied to compression molding tend to react with gabapentin with lapse of time to form 4-cyclohexylpyrrolidone (the corresponding lactam form) by accelerating the dehydration reaction between the amino group and the carboxyl group within the molecule of the compound. This dehydration reaction would be far more accelerated as the compound is being more tightly compressed and would be further accelerated by the use of water or an organic solvent in manufacturing a pharmaceutical preparation, as is the case of gabapentin. It may be said that the mechanism of degradation by the autocondensation is peculiar to the 4-amino-3-substituted-butanoic acid derivatives having a structurally bulky substituent at the 3-position thereof.

To the contrary, in γ-aminobutyric acid derivatives having no or a less bulky substituent at the 3-position thereof, such as γ-aminobutyric acid or 4-amino-3-hydroxy-butanoic acid, the dehydration reaction is not brought about even when maintained in a dried state such as at a temperature of 105° C. over 2-3 hours, and the formation of 4-cyclohexylpyrrolidone (the corresponding lactam form) is not observed. In other words, in the 4-amino-3-substituted-butanoic acid derivative wherein the substituent at the 3-position thereof has a bulky structure, the dehydration reaction could easily be brought about between the amino group and the carboxyl group within the molecule.

In view of the aforesaid background, for drugs which are 4-amino-3-substituted-butanoic acid derivatives, including gabapentin, having a structurally bulky substituent at the 3-position thereof, there have been desired a new pharmaceutical preparation containing said drugs which has an excellent storage stability in the form of liquid preparations or in a small-sized or fluidized dosage form such as tablets or granules for easier ingestion and a process for manufacturing the same.

SUMMARY OF THE INVENTION

We have made earnest studies to solve the prior art problems as stated above and, as a result, have now found that the lactam formation through the intramolecular condensation can be prevented by blocking both the amino group and carboxyl group of a 4-amino-3-substituted-butanoic acid derivative, that it is effective for blocking the amino and carboxyl groups of the 4-amino-3-substituted-butanoic acid derivative to add as a stabilizer an amino acid having a carboxyl group and an amino group within its molecule to the 4-amino-3-substituted-butanoic acid derivative, and that the 4-amino-3-substituted-butanoic acid derivative can possess a superior storage stability not only in the form of its aqueous solution but also in a solid state, on the basis of which this invention has been completed.

DETAILED DESCRIPTION OF THE INVENTION

The present invention relates to a stabilized pharmaceutical preparation containing a 4-amino-3-substituted-butanoic acid derivative which comprises a 4-amino-3-substituted-butanoic acid derivative having the general formula

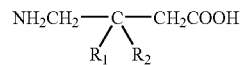

wherein, $R_1$ is a hydrogen atom, a hydroxyl group, a methyl group or an ethyl group;

$R_2$ is a monovalent group selected from:

a straight or branched alkyl group of 3-8 carbon atoms;

a straight or branched alkylene group of 3-8 carbon atoms:

a straight or branched alkyl group of 3-8 carbon atoms which is mono- or di-substituted with a halogen atom, a trifluoromethyl group, a hydroxyl group, an alkoxy group, an alkylthio group, an amino group, a nitro group, an oxo group, a carboxyl group or a carboalkoxy group;

a cycloalkyl group of 3-8 carbon atoms;

a cycloalkyl group of 3-8 carbon atoms which is mono-, di- or tri-substituted with a halogen atom, a trifluoromethyl group, a hydroxyl group, an alkyl group, an alkoxy group, an alkylthio group, an amino group, a nitro group, an oxo group, a carboxyl group or a carboalkoxy group;

a condensed ring group formed by ortho-fusion of a phenyl ring with a cycloalkyl group of 4-8 carbon atoms;

a condensed ring group formed by ortho-fusion of a phenyl ring with a cycloalkyl group of 4-8 carbon atoms wherein said phenyl ring is mono-, di- or tri-substituted with a halogen atom, a trifluoromethyl group, a hydroxyl group, an alkyl group, an alkoxy group, an alkylthio group, an amino group, a nitro group, a carboxyl group or a carboalkoxy group;

a condensed ring group formed by ortho-fusion of a phenyl ring with a cycloalkenyl group of 5-8 carbon atoms or a cycloalkanedienyl group of 5-8 carbon atoms;

a condensed ring group formed by ortho-fusion of a phenyl ring with a cycloalkenyl group of 5-8 carbon atoms or a cycloalkanedienyl group of 5-8 carbon atoms wherein said phenyl ring is mono-, di- or tri-substituted with a halogen atom, a trifluoromethyl group, a hydroxyl group, an alkyl group, an alkoxy group, an alkylthio group, an amino group, a nitro group, a carboxyl group or a carboalkoxy group;

an alkylcycloalkyl group wherein said cycloalkyl has 3-8 carbon atoms and is linked to an alkylene group having 1-4 carbon atoms optionally interrupted with —O—, —S— or —SS—;

an alkylcycloalkyl group wherein said cycloalkyl has 3-8 carbon atoms, is linked to an alkylene group having 1-4 carbon atoms optionally interrupted with —O—, —S— or —SS— and is mono-, di- or tri-substituted with a halogen atom, a trifluoromethyl group, a hydroxyl group, an alkyl group, an alkoxy group, an alkylthio group, an amino group, a nitro group, an oxo group, a carboxyl group or a carboalkoxy group;

a cycloalkyl group of 5-8 carbon atoms wherein one of the methylene groups (—CH$_2$—) is replaced by —O—, —NH—, —S—, —SO— or —S(O)$_2$—;

a cycloalkyl group of 5-8 carbon atoms wherein one of the methylene groups (—CHH$_2$—) is replaced by —O—, —NH—, —S—, —SO— or —S(O)$_2$—, and one or two of the unsubstituted methylene groups (—CH$_2$—) are mono- or di-substituted with a halogen atom, a trifluoromethyl group, a hydroxyl group, an alkyl group, an alkoxy group, an alkylthio group, an amino group, a nitro group, an oxo group, a carboxyl group or a carboalkoxy group;

a cycloalkenyl group of 5-8 carbon atoms or a cycloalkanedienyl group of 5-8 carbon atoms, one of the methylene groups (—CH—) in said cycloalkenyl ring or cycloalkanedienyl ring being replaced by —O—, —NH—, =N—, —S—, —SO— or —S(O)$_2$—;

a cycloalkenyl group of 5-8 carbon atoms or a cycloalkanedienyl group of 5-8 carbon atoms, one of the methylene groups (—CH$_2$—) in said cycloalkenyl ring or cycloalkanedienyl ring being replaced by —O—, —NH—, =N—, —S—, —SO— or —S(O)$_2$—, and one or two of the unsubstituted methylene groups (—CH$_2$—) being mono- or di-substituted with a halogen atom, a trifluoromethyl group, a hydroxyl group, an alkyl group, an alkoxy group, an alkylthio group, an amino group, a nitro group, an oxo group, a carboxyl group or a carboalkoxy group;

a condensed ring group formed by ortho-fusion of a phenyl ring with a cycloalkyl group of 5-8 carbon atoms wherein one of the methylene groups (—CHH$_2$—) is replaced by —O—, —NH—, —S—, —SO— or —S(O)$_2$—;

a condensed ring group formed by ortho-fusion of a phenyl ring with a cycloalkyl group of 5-8 carbon atoms wherein one of the methylene groups (—CH$_2$—) is replaced by —O—, —NH—, —S—, —SO— or —S(O)$_2$—, said phenyl group being mono- or di-substituted with a halogen atom, a trifluoromethyl group, a hydroxyl group, an alkyl group, an alkoxy group, an alkylthio group, an amino group, a nitro group, a carboxyl group or a carboalkoxy group;

a condensed ring group formed by ortho-fusion of a phenyl ring with a cycloalkenyl group of 5-8 carbon atoms or a cycloalkanedienyl group of 5-8 carbon atoms, one of the methylene groups (—CH$_2$—) in said cycloalkenyl ring or cycloalkanedienyl ring being replaced by —O—, —NH—, =N—, —S—, —SO— or —S(O)$_2$—;

a condensed ring group formed by ortho-fusion of a phenyl ring with a cycloalkenyl group of 5-8 carbon atoms or a cycloalkanedienyl group of 5-8 carbon atoms, one of the methylene groups (—CH$_2$—) in said cycloalkenyl ring or cycloalkanedienyl ring being replaced by —O—, —NH—, =N—, —S—, —SO— or —S(O)$_2$—, said phenyl ring being mono- or di-substituted with a halogen atom, a trifluoromethyl group, a hydroxyl group, an alkyl group, an alkoxy group, an alkylthio group, an amino group, a nitro group, a carboxyl group or a carboalkoxy group;

an alkylcycloalkyl group wherein said cycloalkyl has 5-8 carbon atoms and is linked to an alkylene group having 1-4 carbon atoms optionally interrupted with —O—, —S— or —SS—, one of the methylene groups (—CH$_2$—) in said cycloalkyl ring being replaced by —O—, —NH—, —S—, —SO— or —S(O)$_2$—;

an alkylcycloalkyl group wherein said cycloalkyl has 5-8 carbon atoms and is linked to an alkylene group having 1-4 carbon atoms optionally interrupted with —O—, —S— or —SS—, and one of the methylene groups (—CH$_2$—) in said cycloalkyl ring being replaced by —O—, —NH—, —S—, —SO— or —S(O)$_2$— and one or two of the unsubstituted methylene groups (—CH$_2$—) being mono-, di- or tri-substituted with a halogen atom, a trifluoromethyl group, a hydroxyl group, an alkyl group, an alkoxy group, an alkylthio group, an amino group, a nitro group, an oxo group, a carboxyl group or a carboalkoxy group;

a phenyl or naphthyl group;

a phenyl group substituted with a methylenedioxy group;

a phenyl or naphthyl group which is mono-, di- or tri-substituted with a halogen atom, a trifluoromethyl group, a hydroxyl group, an alkyl group, an alkoxy group, an amino group, a nitro group, a carboxyl group, a phenoxy group, a phenylmethoxy group, a phenylmethoxy group wherein said phenyl ring is mono-substituted with a halogen atom, trifluoromethyl group, an alkoxy group, an amino group, a nitro group, a carboxyl group or a carboalkoxy group, a cycloalkylmethoxy group having 5-8 carbon atoms in the cycloalkyl ring, a cycloalkenylmethoxy group having 5-8 carbon atoms in the cycloalkenyl ring, a cycloalkanedienylmethoxy group having 5-8 carbon atoms in the cycloalkanedienyl ring, a cycloalkylmethoxy group wherein one of the methylene groups (—CH$_2$—) in said cycloalkyl ring having 5-8 carbon atoms is replaced by —O—, —NH—, —S—, —SO— or —S(O)$_2$—, a cycloalkenylmethoxy group wherein one of the methylene groups (—CH$_2$—) in said cycloalkenyl ring having 5-8 carbon atoms is replaced by —O—, —NH—, =N—, —S—, —SO— or —S(O)$_2$—, a cycloalkanedienyl-methoxy group wherein one of the methylene groups (—CH$_2$—) in said cycloalkanedienyl ring having 5-8 carbon atoms is replaced by —O—, —NH—, =N—, —S—, —SO— or —S(O)$_2$— group, a cycloalkylmethoxy group having 5-8 carbon atoms in the cycloalkyl ring wherein said cycloalkyl ring is mono-substituted with a halogen atom, trifluoromethyl group, a hydroxy group, an alkyl group, an alkoxy group, an amino group, a nitro group, a carboxyl group or a carboalkoxy group and one of the methylene groups (—CH$_2$—) in said cycloalkyl ring is replaced by —O—, —NH—, —S—, —SO— or —S(O)$_2$—, a cycloalkenylmethoxy group having 5-8 carbon atoms in the cycloalkenyl ring wherein said cycloalkenyl ring is mono-substituted with a halogen atom, a trifluoromethyl group, a hydroxy group, an alkyl group, an alkoxy group, an amino group, a nitro group, an oxo group, a carboxyl group or a carboalkoxy group and one of the methylene groups (—CH$_2$—) in said cycloalkenyl ring is replaced by —O—, —NH—, =N—, —S—, —SO— or —S(O)$_2$—, or a cycloalkanedienylmethoxy group having 5-8 carbon atoms in the cycloalkanedienyl ring wherein said cycloalkanedienyl ring is mono-substituted with a halogen atom, a trifluoromethyl group, a hydroxyl group, an alkyl group, an alkoxy group, an amino group, a nitro group, an oxo group, a carboxyl group or a carboalkoxy group and one of the methylene groups (—CH$_2$—) in said cycloalkanedienyl ring is replaced by —O—, —NH—, =N—, —S—, —SO— or —S(O)$_2$—;

an alkylphenyl group wherein said phenyl group is linked to an alkylene group having 1-4 carbon atoms optionally interrupted with —O—, —S— or —SS—;

an alkyl-O—, —S— or —SS-phenyl group wherein said phenyl group is linked to an alkylene group having 1-4 carbon atoms via —O—, —S— or —SS—;

an —O—, —S— or —SS-phenyl group;

a diphenylamino group;

an alkylphenyl group wherein said phenyl group is linked to an alkylene group having 1-4 carbon atoms optionally interrupted with —O—, —S— or —SS— and mono-, di- or tri-substituted with a halogen atom, a trifluoromethyl group, a hydroxyl group, a alkyl group, an alkoxy group, an amino group, a nitro group or a carboxyl group;

an alkyl-O—, —S— or —SS-phenyl group wherein said phenyl group is linked to an alkylene group having 1-4 carbon atoms via —O—, —S— or —SS— and mono-, di- or tri-substituted with a halogen atom, a trifluoromethyl group, a hydroxyl group, an alkyl group, an alkoxy group, an amino group, a nitro group or a carboxyl group;

an —O—, —S— or —SS-phenyl group wherein said phenyl group is mono-, di- or tri-substituted with a halogen atom, a trifluoromethyl group, a hydroxyl group, an alkyl group, an alkoxy group, an amino group, a nitro group or a carboxyl group;

or

R$_1$ and R$_2$, together with the carbon atom to which they are attached, may form a divalent group selected from:

a cycloalkylidene group of 5-8 carbon atoms;

a cycloalkylidene group of 5-8 carbon atoms which is mono-, di-, tri- or tetra-substituted with a halogen atom, a trifluoromethyl group, a hydroxyl group, an alkyl group, an alkoxy group, an alkylthio group, a cycloalkyl group, a phenyl group, an amino group, a nitro group or a carboxyl group;

a cycloalkylidene group of 5-8 carbon atoms wherein one of the methylene groups (—CH$_2$—) in said cycloalkyl ring is replaced by —O—, —NH—, —S—, —SO— or —S(O)$_2$—;

a cycloalkylidene group of 5-8 carbon atoms wherein one of the methylene groups (—CH—) in said cycloalkyl ring is replaced by —O—, —NH—, —S—, —SO— or —S(O)$_2$— group and one or more of the unsubstituted methylene groups (—CH$_2$—) in said cycloalkyl ring are mono-, di-, tri- or tetra-substituted with a halogen atom, a trifluoromethyl group, a hydroxyl group, an alkyl group, an alkoxy group, an alkylthio group, an amino group, a nitro group, an oxo group, a carboxyl group or a carboalkoxy group;

a cycloalkenylidene group of 5-8 carbon atoms or a cycloalkanedienylidene group of 5-8 carbon atoms;

a cycloalkenylidene group of 5-8 carbon atoms or a cycloalkanedienylidene group of 5-8 carbon atoms which is mono-, di-, tri- or tetra-substituted with a halogen atom, a trifluoromethyl group, a hydroxyl group, an alkyl group, an alkoxy group, an alkylthio group, a cycloalkyl group, a phenyl group, an amino group, a nitro group, an oxo group, a carboxyl group or a carboalkoxy group;

a cycloalkenylidene group of 5-8 carbon atoms or a cycloalkanedienylidene group of 5-8 carbon atoms wherein one of the methylene groups (—CH$_2$—) in said cycloalkenyl ring or cycloalkanedienyl ring is replaced by —O—, —NH—, =N—, —S—, —SO— or —S(O)$_2$—;

a cycloalkenylidene group of 5-8 carbon atoms or a cycloalkanedienylidene group of 5-8 carbon atoms wherein one of the methylene groups (—CH$_2$—) in said cycloalkenyl ring or cycloalkanedienyl ring is replaced by —O—, —NH—, =N—, —S—, —SO— or —S(O)$_2$— group and one or more of the unsubstituted methylene groups (—CH$_2$—) in said cycloalkenyl ring or cycloalkanedienyl ring are mono-, di-, tri- or tetra-substituted with a halogen atom, a trifluoromethyl group, a hydroxyl group, an alkyl group, an alkoxy group, an alkylthio group, an amino group, a nitro group, an oxo group, a carboxyl group or a carboalkoxy group;

a condensed ring group formed by ortho-fusion of a phenyl ring with a cycloalkylidene group of 4-8 carbon atoms;

a condensed ring group formed by ortho-fusion of a phenyl ring with a cycloalkylidene group of 4-8 carbon atoms, said phenyl ring being mono-, di-, tri- or tetra-substituted with a halogen atom, a trifluoromethyl group, a hydroxyl group, an alkyl group, an alkoxy group, an alkylthio group, an amino group, a nitro group, a carboxyl group or a carboalkoxy group;

a condensed ring group formed by ortho-fusion of a phenyl ring with a cycloalkenylidene group of 5-8 carbon atoms or a cycloalkanedienylidene group of 5-8 carbon atoms;

a condensed ring group formed by ortho-fusion of a phenyl ring with a cycloalkenylidene group of 5-8 carbon atoms or a cycloalkanedienylidene group of 5-8 carbon atoms, said phenyl ring being mono- or di-substituted with a halogen atom, a trifluoromethyl group, a hydroxyl group, an alkyl group, an alkoxy group, an alkylthio group, an amino group, a nitro group, a carboxyl group or a carboalkoxy group;

an α-amino acid; and, if necessary, an auxiliary agent for manufacturing a pharmaceutical preparation.

The invention also relates to a stabilized liquid pharmaceutical preparation containing a 4-amino-3-substituted-butanoic acid derivative.

The invention also relates to the stabilized liquid pharmaceutical preparation in the dosage form of liquid preparations, syrups or injections.

The invention also relates to a stabilized solid pharmaceutical preparation containing a 4-amino-3-substituted-butanoic acid derivative.

The invention also relates to the stabilized solid pharmaceutical preparation in the dosage form of tablets, powders, granules or capsules.

Also, the invention relates to a process for the preparation of a pharmaceutical preparation containing a 4-amino-3-substituted-butanoic acid derivative which comprises combining a 4-amino-3-substituted-butanoic acid derivative having the following formula

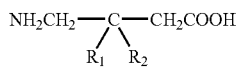

(wherein $R_1$ and $R_2$ are as defined above) with an amino acid as a stabilizer and, if necessary, an auxiliary agent for manufacturing a pharmaceutical preparation.

The invention further relates to a process for the preparation of a stabilized pharmaceutical preparation containing a 4-amino-3-substituted-butanoic acid derivative which is in a solid or liquid form.

The 4-amino-3-substituted-butanoic acid derivatives which may be stabilized according to the present invention include those compounds as listed in the following Tables 1 and 2:

TABLE 1

| $NH_2CH_2-C(R_1)(R_2)-CH_2COOH$ | |
|---|---|
| —$R_1$ | —$R_2$ |
| —H | —$CH_2$—$CH_2$—$CH_3$ |
| —H | —$CH(CH_3)_2$ |
| —H | —$CH_2$—$CH_2$—$CH_2$—$CH_3$ |
| —H | —$CH_2$—$CH(CH_3)_2$ |
| —H | —$C(CH_2)_3$ |
| —H | —$(CH_2)_4$—$CH3$ |
| —H | —$(CH_2)_3$—$CH$—$(CH_3)_2$ |
| —H | —$CH(CH_2$—$CH_3)(CH_3)$ |
| —H | —$CH_2$—$CH_2$—$CH_2NH_2$ |
| —H | —$CH_2$—$CH_2$—$CH_2$—$CH_2$—$NH_2$ |
| —H | —$CH_2$—$CH_2$—$CH_2Cl$ |
| —H | —$CH_2$—$CH_2$—$CH_2OH$ |

TABLE 1-continued

| $NH_2CH_2-C(R_1)(R_2)-CH_2COOH$ | |
|---|---|
| —$R_1$ | —$R_2$ |
| —H | —$CH_2$—$CH_2$—$CH_2$—$CH_2$—Cl |
| —H | —$CH_2$—$CH_2$—$CH_2Br$ |
| —H | —$CH_2$—$CH_2$—$CH_2I$ |
| —H | —$CH_2$—$CH(CH_3)$—$CHCl$ |
| —H | —$CH_2$—$CO$—$CH_3$ |
| —H | —$CH_2$—$CH_2$—$CO$—$CH_3$ |
| —H | —$CH_2$—$CH_2$—$CH_2$—$CHOH$ |
| —H |  |
| —H | 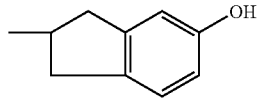 |
| —H | 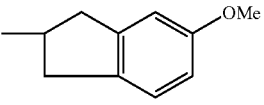 |
| —H | 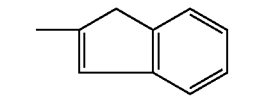 |
| —H | 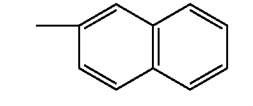 |
| —H | 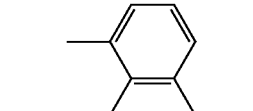 |
| —H | 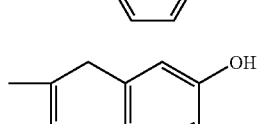 |
| —H | 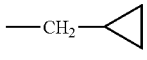 |
| —H | —$CH_2$— 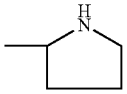 |
| —H |  |

TABLE 1-continued $$NH_2CH_2-\underset{\underset{R_2}{\overset{\overset{R_1}{|}}{C}}}{}-CH_2COOH$$

| —$R_1$ | —$R_2$ |
|---|---|
| —H | 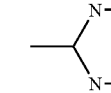 |
| —H | 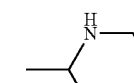 |
| —H | 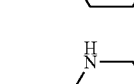 |
| —H | 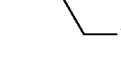 |
| —H | 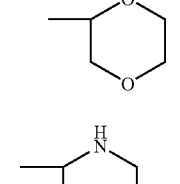 |
| —H | 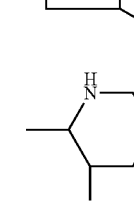 |
| —H | 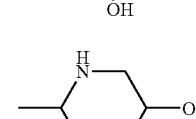 |
| —H | 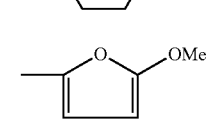 |
| —H | 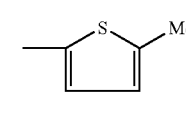 |
| —H | 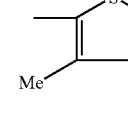 |
| —H | 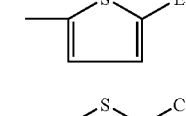 |
| —H | (see continuation) |

TABLE 1-continued $$NH_2CH_2-\underset{\underset{R_2}{\overset{\overset{R_1}{|}}{C}}}{}-CH_2COOH$$

| —$R_1$ | —$R_2$ |
|---|---|
| —H | (thiophene with Cl) |
| —H | (thiophene with Cl) |
| —H | (thiophene with Br) |
| —H | (thiophene with Br) |
| —H | (quinoxaline) |
| —H | (benzofuran) |
| —H | (benzofuran with OMe) |
| —H | (benzofuran with OMe) |
| —H | (benzofuran with OMe) |
| —H | (benzofuran with Et) |
| —H | (benzofuran with Cl) |
| —H | (benzofuran with Cl) |

TABLE 1-continued

NH₂CH₂—C(R₁)(R₂)—CH₂COOH

| —R₁ | —R₂ |
|---|---|
| —H | 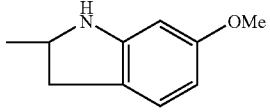 (2-methyl-6-methoxyindoline) |
| —H | 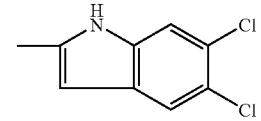 (2-methyl-5,6-dichloroindole) |
| —H | 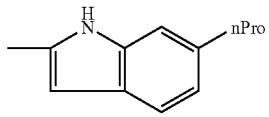 (2-methyl-6-nPro-indole) |
| —H | 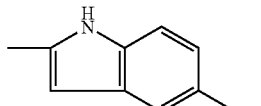 (2-methyl-5-nPro-indole) |
| —H | 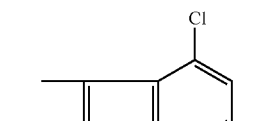 (3-methyl-4-chloroindole) |
| —H | 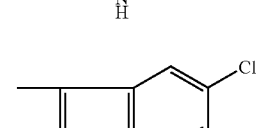 (3-methyl-5-chloroindole) |
| —H | 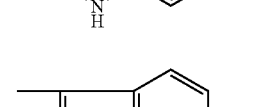 (3-methyl-6-chloroindole) |
| —H | 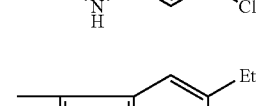 (3-methyl-5-ethylindole) |
| —H | 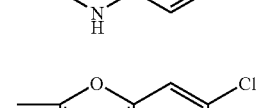 (2-methyl-6-chlorobenzofuran) |
| —H | 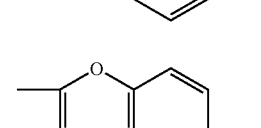 (2-methyl-5-chlorobenzofuran) |
| —H |  (2-methyl-4,6-dichlorobenzofuran) |
| —H |  (2-methyl-5-bromobenzofuran) |
| —H | 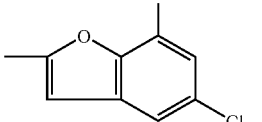 (2-methyl-4-chloro-6-methylbenzofuran) |
| —H | 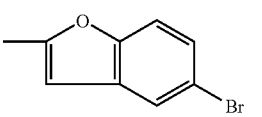 (2-methyl-7-Me-5-Cl-benzofuran) |
| —H | 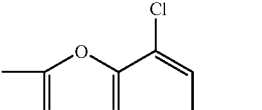 (2-methyl-7-methylbenzofuran) |
| —H | 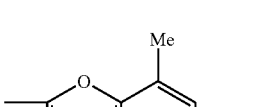 (2-methyl-6-methylbenzofuran) |
| —H | 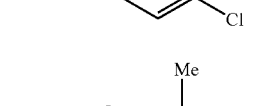 (2-methyl-5,6-dimethylbenzofuran) |
| —H | 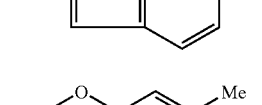 (2-methyl-7-OEt-benzofuran) |
| —H | 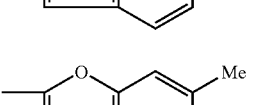 (2-methyl-5-OEt-benzofuran) |
| —H | 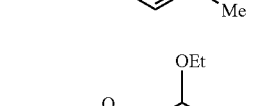 (2-methyl-5-OnBu-benzofuran) |

TABLE 1-continued
$$\text{NH}_2\text{CH}_2\underset{\underset{R_2}{|}}{\overset{\overset{R_1}{|}}{C}}\text{CH}_2\text{COOH}$$
| —R₁ | —R₂ |
|---|---|
| —H | 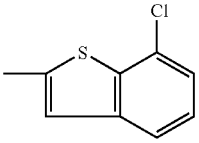 |
| —H | 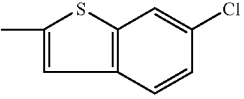 |
| —H | 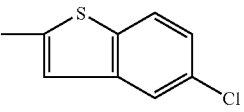 |
| —H | 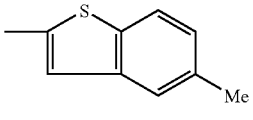 |
| —H | 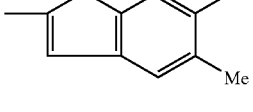 |
| —H | 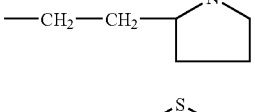 |
| —H | 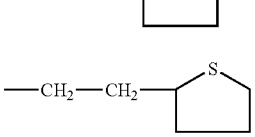 |
| —H | 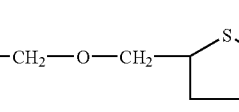 |
| —H | 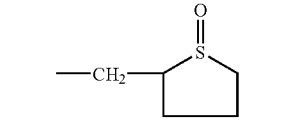 |
| —H | 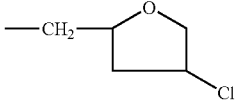 |
| —H | 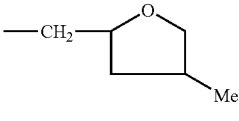 |
TABLE 1-continued
$$\text{NH}_2\text{CH}_2\underset{\underset{R_2}{|}}{\overset{\overset{R_1}{|}}{C}}\text{CH}_2\text{COOH}$$
| —R₁ | —R₂ |
|---|---|
| —H | 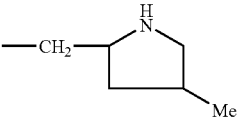 |
| —H | 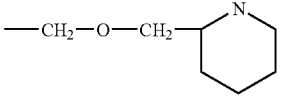 |
| —H | 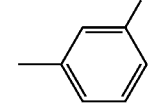 |
| —H | 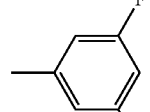 |
| —H | 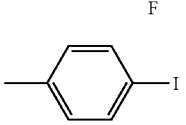 |
| —H | 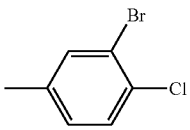 |
| —H | 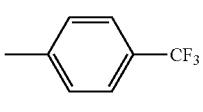 |
| —H | 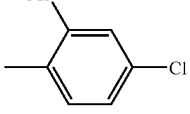 |
| —H | 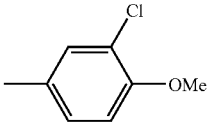 |
| —H | 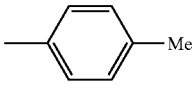 |
| —H | 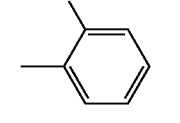 |

TABLE 1-continued $$NH_2CH_2-\underset{\underset{R_2}{|}}{\overset{\overset{R_1}{|}}{C}}-CH_2COOH$$

| —R₁ | —R₂ |
|---|---|
| —H | 3,5-dimethylphenyl |
| —H | 4-hydroxy-3-methoxyphenyl (with 2-OMe, 4-OH pattern shown) |
| —H | 3-methoxyphenyl |
| —H | 2-methoxyphenyl |
| —H | 4-methoxyphenyl |
| —H | 3,4,5-trimethoxyphenyl |
| —H | 4-isopropoxyphenyl |
| —H | 3,4-dimethoxyphenyl |
| —H | 2,3,6-trimethoxyphenyl (MeO, OMe, OMe pattern) |
| —H | 3-methoxy-4-tert-butoxyphenyl |
| —H | benzo[1,3]dioxol-4-yl |
| —H | —CH₂—NH—C₆H₅ |
| —H | —CH₂—N(C₆H₅)₂ |
| —H | —CH₂—O—CH₂—(3,4-dichlorophenyl) |
| —H | —CH₂—S—CH₂—(3,4-dichlorophenyl) |
| —H | —CH₂—S—CH₂—(4-methylphenyl) |
| —H | —CH₂—S—CH₂—CH₂—(2,4-dichlorophenyl) |
| —H | —CH₂—S—CH₂—CH₂—(4-chlorophenyl) |
| —H | —CH₂—CH₂—O—CH₂—(4-aminophenyl) |
| —H | —CH₂—CH₂—S—CH₂—(3,4-dichlorophenyl) |
| —H | —CH₂—CH₂—S—CH₂—(4-bromophenyl) |
| —OH | —CH₂—C(CH₃)₃ |
| —OH | —CH₂—CH₂—CH₃ |
| —OH | —CH₂—CH₂—CH₂—CH₃ |
| —OH | —CH₂—CH(CH₃)₂ |

TABLE 1-continued
$$NH_2CH_2-\underset{\underset{R_2}{|}}{\overset{\overset{R_1}{|}}{C}}-CH_2COOH$$
| —R$_1$ | —R$_2$ |
|---|---|
| —OH | 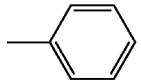 |
| —OH |  |
| —OH | 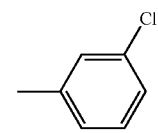 |
| —OH | 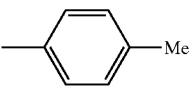 |
| —OH | —CH$_2$—O—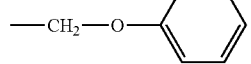 |
| —OH | 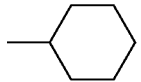 |
| —OH | 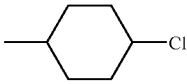 |
| —OH | 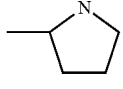 |
| —OH |  |
| —OH |  |
| —CH$_3$ | —CH$_2$—CH$_2$—CH$_3$ |
| —H | —CH=CH—CH$_3$ |
| —H | —CH=CH—CH$_2$—CH$_3$ |
| —H | —C(CH$_3$)=CH—CH$_3$ |
| —H | —CH=C(CH$_3$)$_2$ |
| —H | 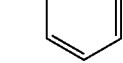 |
| —H | 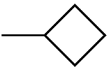 |
TABLE 1-continued
$$NH_2CH_2-\underset{\underset{R_2}{|}}{\overset{\overset{R_1}{|}}{C}}-CH_2COOH$$
| —R$_1$ | —R$_2$ |
|---|---|
| —H | 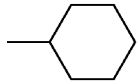 |
| —H | 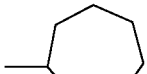 |
| —H | 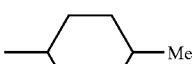 |
| —H | 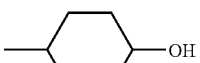 |
| —H | 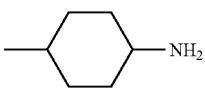 |
| —H | 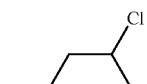 |
| —H | 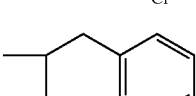 |
| —H | 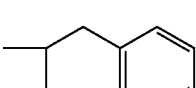 |
| —H | 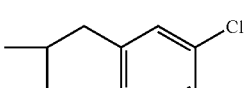 |
| —H | 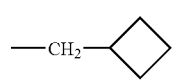 |
| —H | —CH$_2$—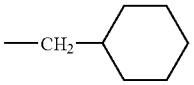 |
| —H | —CH$_2$—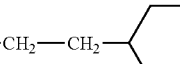 |
| —H | —CH$_2$—CH$_2$—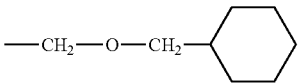 |
| —H | —CH$_2$—O—CH$_2$— |

TABLE 1-continued $$NH_2CH_2-\underset{\underset{R_2}{|}}{\overset{\underset{R_1}{|}}{C}}-CH_2COOH$$

| —$R_1$ | —$R_2$ |
|---|---|
| —H | —CH$_2$—(cyclohexyl)—OH |
| —H | —CH$_2$—(cyclohexyl with OH) |
| —H | —CH$_2$—(cyclohexyl)—OMe |
| —H | —CH$_2$—(cyclohexyl)—Cl |
| —H | —CH$_2$—O—CH$_2$—(cyclohexyl)—OH |
| —H | 2-tetrahydrofuranyl |
| —H | piperazinyl-OH |
| —H | dihydrothienyl |
| —H | 2-furyl |
| —H | 2-thienyl |
| —H | 2-imidazolyl |
| —H | 2-pyridyl |
| —H | 1,4-dioxinyl |
| —H | 2-pyrazinyl |
| —H | 2,5-dimethylfuran (5-methyl-2-furyl with CH$_3$) |
| —H | 3-bromo-2-thienyl |
| —H | 3-hydroxy-2-pyridyl |
| —H | 5-hydroxy-2-pyridyl |
| —H | 2-benzofuranyl |
| —H | 2-benzothienyl |
| —H | 2-indolyl |
| —H | 3-indolyl |
| —H | 2-quinolinyl |
| —H | 2H-chromenyl |
| —H | 5-methoxy-2-indolinyl |

TABLE 1-continued $NH_2CH_2-\underset{\underset{R_1}{|}\ \underset{R_2}{|}}{C}-CH_2COOH$

| —$R_1$ | —$R_2$ |
|---|---|
| —H | 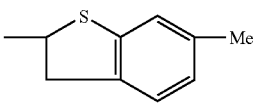 2-methyl-6-methyl-2,3-dihydrobenzothiophene |
| —H | 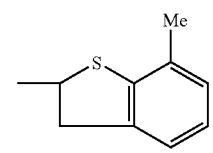 2-methyl-7-methyl-2,3-dihydrobenzothiophene |
| —H | 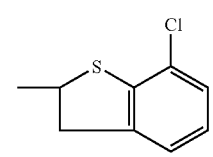 2-methyl-7-chloro-2,3-dihydrobenzothiophene |
| —H | 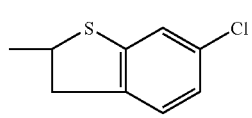 2-methyl-6-chloro-2,3-dihydrobenzothiophene |
| —H | 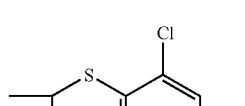 2-methyl-5,7-dichloro-2,3-dihydrobenzothiophene |
| —H | 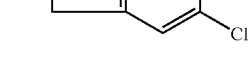 2-methyl-6-bromo-2,3-dihydrobenzothiophene |
| —H | 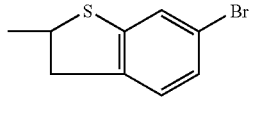 2-methyl-7-chloroindole |
| —H | 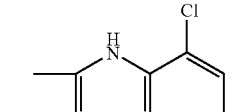 2-methyl-6-chloroindole |
| —H | 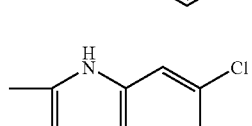 2-methyl-5,6-dihydroxyindole |
| —H | 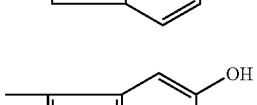 2-methyl-5,6-dimethoxybenzofuran |

TABLE 1-continued $NH_2CH_2-\underset{\underset{R_1}{|}\ \underset{R_2}{|}}{C}-CH_2COOH$

| —$R_1$ | —$R_2$ |
|---|---|
| —H | 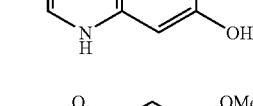 2-methyl-7-methoxybenzofuran |
| —H | 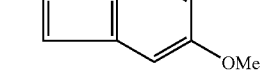 2-methyl-6-methoxybenzofuran |
| —H | 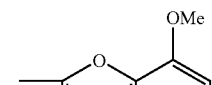 2-methyl-5-methoxybenzofuran |
| —H | 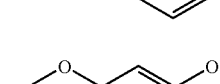 2-methyl-6-fluorobenzofuran |
| —H | 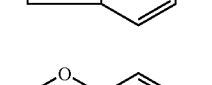 2-methyl-5,7-difluorobenzofuran |
| —H | 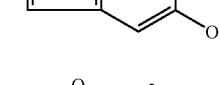 2-methyl-5-fluorobenzofuran |
| —H | 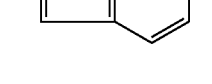 2-methyl-7-chlorobenzofuran |
| —H | 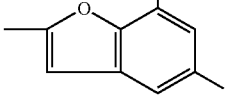 2-methyl-7-ethylbenzofuran |
| —H | 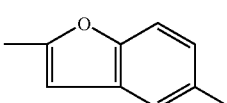 2-methyl-6-ethylbenzofuran |
| —H |  2-methyl-5-ethylbenzofuran |

TABLE 1-continued $$NH_2CH_2-\underset{\underset{R_2}{|}}{\overset{\overset{R_1}{|}}{C}}-CH_2COOH$$

| —$R_1$ | —$R_2$ |
|---|---|
| —H | 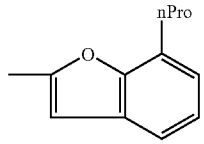 (2-methyl-7-nPro-benzofuran) |
| —H | 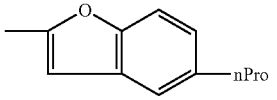 (2-methyl-5-nPro-benzofuran) |
| —H | 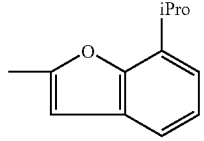 (2-methyl-7-iPro-benzofuran) |
| —H | 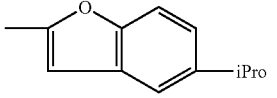 (2-methyl-5-iPro-benzofuran) |
| —H | 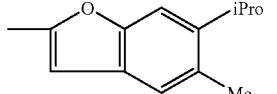 (2-methyl-6-iPro-5-Me-benzofuran) |
| —H | 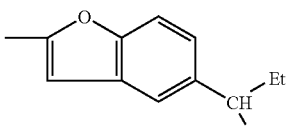 (2-methyl-5-(CH(Et)Me)-benzofuran) |
| —H | 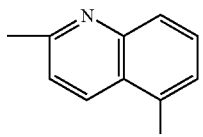 (2-methyl-5-CO$_2$H-quinoline) |
| —H | 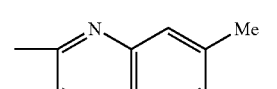 (2-methyl-7-Me-quinoline) |
| —H | 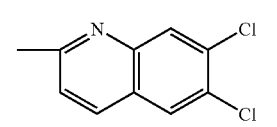 (2-methyl-6,7-diCl-quinoline) |
| —H | —CH$_2$-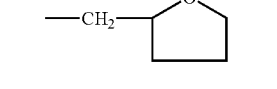 (tetrahydrofuran-2-yl) |
| —H | —CH$_2$—CH$_2$- |

TABLE 1-continued $$NH_2CH_2-\underset{\underset{R_2}{|}}{\overset{\overset{R_1}{|}}{C}}-CH_2COOH$$

| —$R_1$ | —$R_2$ |
|---|---|
| —H | —CH$_2$- (tetrahydropyran-2-yl) |
| —H | —CH$_2$-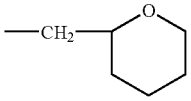 (1,4-dioxan-2-yl) |
| —H | —CH$_2$—O—CH$_2$-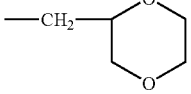 |
| —H | —CH$_2$-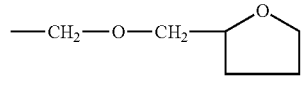 (pyrrolidin-2-yl) |
| —H | 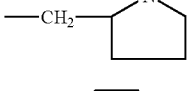 (phenyl) |
| —H |  (3-NH$_2$-phenyl) |
| —H | 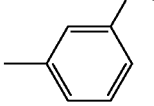 (4-NH$_2$-phenyl) |
| —H | 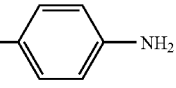 (4-Cl-phenyl) |
| —H | 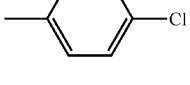 (3-Cl-phenyl) |
| —H | 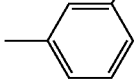 (2,3-diCl-phenyl) |
| —H | 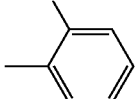 (3,4-diCl-phenyl) |
| —H | 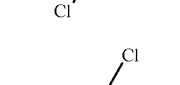 (2,4-diCl-phenyl) |

TABLE 1-continued $$NH_2CH_2-\underset{\underset{R_2}{|}}{\overset{\overset{|}{C}}{|}}-CH_2COOH$$

| —R₁ | —R₂ |
|---|---|
| —H | 4-F-C₆H₄— |
| —H | 2,3,5-trimethylphenyl— |
| —H | 4-Et-C₆H₄— |
| —H | 4-nPro-C₆H₄— |
| —H | 4-iPro-C₆H₄— |
| —H | 4-OMe-C₆H₄— |
| —H | 2,4-diOMe-C₆H₃— |
| —H | 2-Me-4-OMe-C₆H₃— (OMe at 1, Me at 4, attachment at... see structure) |
| —H | 4-OH-C₆H₄— |
| —H | 3-OH-C₆H₄— |
| —H | 2-OH-C₆H₄— |
| —H | benzo[1,3]dioxol-5-yl |
| —H | 3-phenoxyphenyl— |
| —H | 4-phenoxyphenyl— |
| —H | 4-(benzyloxy)phenyl— |
| —H | 4-((5-chlorothiophen-2-yl)methoxy)phenyl— |
| —H | —CH₂—O—CH₂—C₆H₅ |
| —H | —CH₂—CH₂—S—CH₂—C₆H₅ |
| —H | —CH₂—C₆H₅ |
| —H | —CH₂—CH₂—C₆H₅ |
| —H | —CH₂—S—C₆H₅ |
| —H | —CH₂—O—(4-tBu-C₆H₄) |
| —H | —CH₂—S—(4-Br-C₆H₄) |
| —H | —CH₂—CH₂—S—(4-CF₃-C₆H₄) |
| —H | —O—(4-Cl-C₆H₄) |

TABLE 1-continued

NH₂CH₂—C(R₁)(R₂)—CH₂COOH

| —R₁ | —R₂ |
|---|---|
| —H | 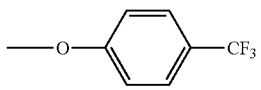 —O—C₆H₄—CF₃ |
| —H | 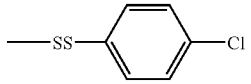 —SS—C₆H₄—Cl |
| —H | 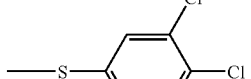 —S—C₆H₃(Cl)(Cl) |
| —H | 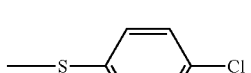 —S—C₆H₄—Cl |
| —H |  (1-methylcytosin-4-amino) |
| —H | 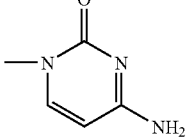 (hexahydrobenzoxazolone-Me) |
| —CH₃ | —CH(CH₃)₂ |
| —CH₃ | —CH₂—CH(CH₃)₂ |
| —CH₃ | —CH₂—CH₂—CH₂—CH₃ |
| —CH₃ | 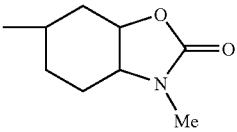 phenyl |
| —CH₃ | 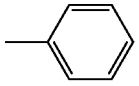 4-Cl-phenyl |
| —CH₃ | 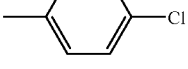 —CH₂-phenyl |
| —CH₃ | 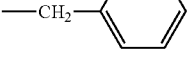 —CH₂-cyclohexyl |
| —CH₂—CH₃ | —CH₂—CH(CH₃)₂ |
| —CH₃ | 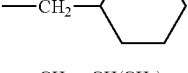 phenyl |
| —CH₂—CH₃ | 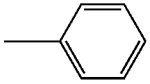 —CH₂-phenyl |

TABLE 1-continued

NH₂CH₂—C(R₁)(R₂)—CH₂COOH

| —R₁ | —R₂ |
|---|---|
| —CH₂—CH₃ | 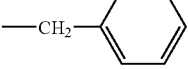 4-Cl-phenyl |
| —CH₂—CH₃ |  —CH₂-(4-Cl-phenyl) |
| —CH₂—CH₃ | 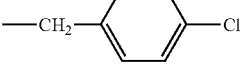 tetrahydrofuryl |
| —CH₂—CH₃ |  furyl |
| —CH₂—CH₃ |  pyridyl |
| —H | —CH=CH—CH₂—CH₂—CH₃ |
| —H | —CH=CH—CH(CH₃)₂ |

TABLE 2

NH₂CH₂—C(R₁)(R₂)—CH₂COOH

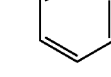

| |
|---|
|  |
|  |
|  |
| 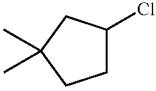 |
| 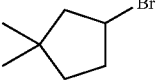 |
| 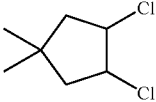 |

TABLE 2-continued
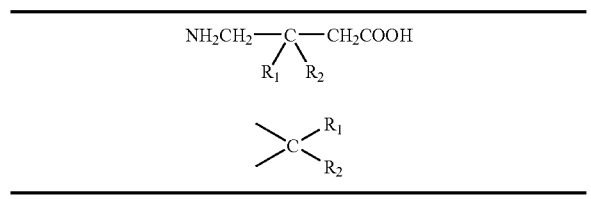
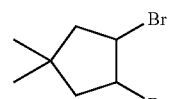
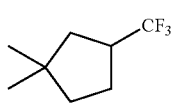
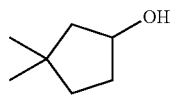
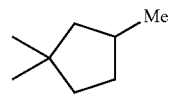
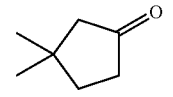
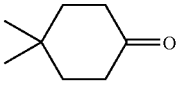
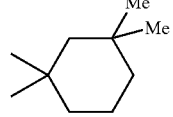
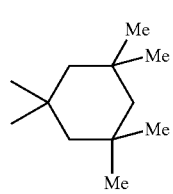
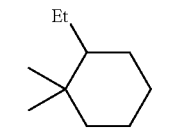
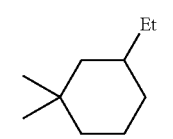
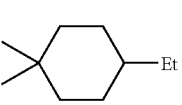
TABLE 2-continued
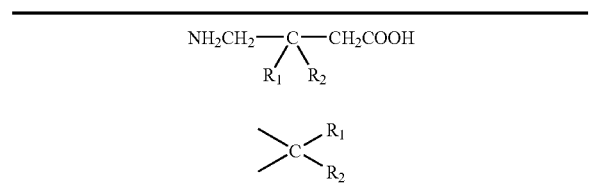
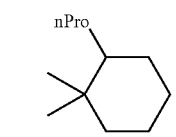
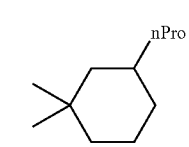
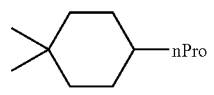
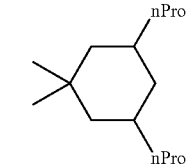
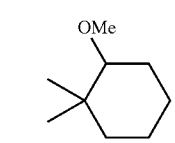
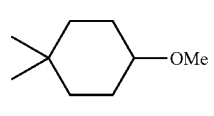
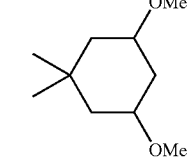
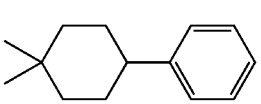

TABLE 2-continued $$NH_2CH_2-\underset{\underset{R_2}{|}}{\overset{\overset{R_1}{|}}{C}}-CH_2COOH$$

$$\underset{\underset{R_2}{|}}{\overset{\overset{R_1}{|}}{-C-}}$$

TABLE 2-continued
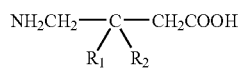
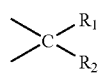
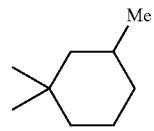
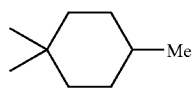
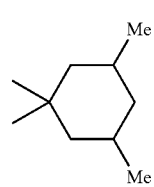
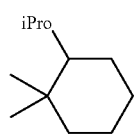
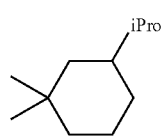
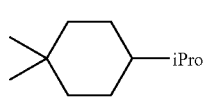
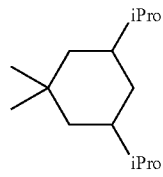
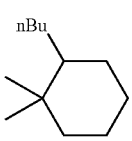
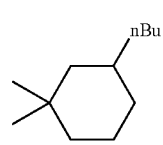
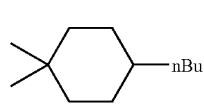
TABLE 2-continued
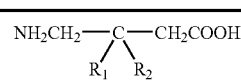
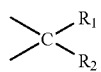
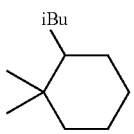
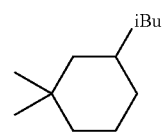
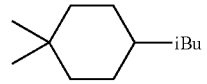
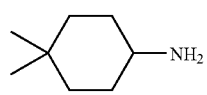
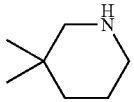
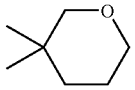
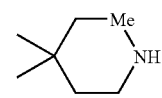
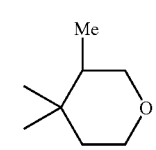

TABLE 2-continued

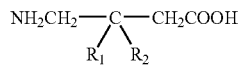
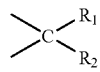

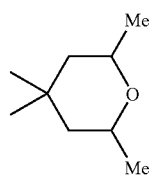
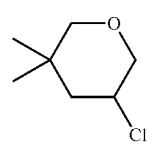
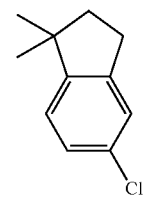
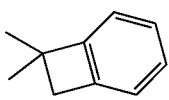
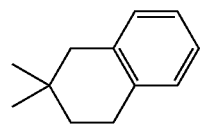
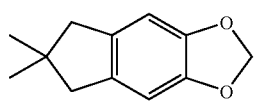
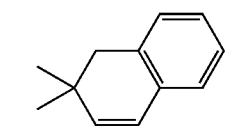
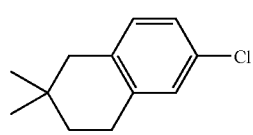
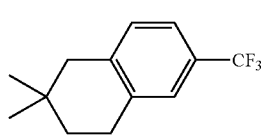
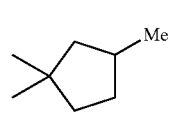

TABLE 2-continued

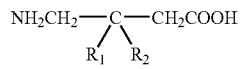

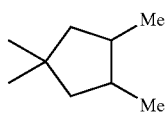

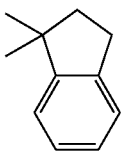

The present invention provides an extremely effective stabilizing means in manufacturing a pharmaceutical preparation containing a 4-amino-3-substituted-butanoic acid derivative having a bulky substituent at the 3-position thereof as explained above, and the means of the invention is extremely effective in stabilizing these compounds in preparing a pharmaceutical preparation of, for example, gabapentin, pregabalin, baclofen, 3-aminomethyl-4-cyclohexyl-butanoic acid, 3-aminomethyl-5-cyclohexyl-pentanoic acid, 3-aminomethyl-4-phenyl-butanoic acid, 3-aminomethyl-5-phenyl-pentanoic acid, etc.

The present invention relates to a stabilized pharmaceutical preparation containing a 4-amino-3-substituted-butanoic acid derivative which comprises the 4-amino-3-substituted-butanoic acid derivative, an amino acid as a stabilizer and, if necessary, an auxiliary agent for manufacturing a pharmaceutical preparation.

The invention also relates to a stabilized pharmaceutical preparation containing a 4-amino-3-substituted-butanoic acid derivative in a liquid or solid form.

The invention also relates to a stabilized liquid pharmaceutical preparation containing a 4-amino-3-substituted-butanoic acid derivative in the dosage form of liquid preparations, syrups or injections.

The invention also relates to a stabilized solid pharmaceutical preparation containing a 4-amino-3-substituted-butanoic acid derivative.

The invention also relates to a stabilized solid pharmaceutical preparation containing a 4-amino-3-substituted-butanoic acid derivative in the dosage form of tablets, powders, granules or capsules.

Also, the invention relates to a process for the preparation of a stabilized pharmaceutical preparation containing a 4-amino-3-substituted-butanoic acid derivative which comprises combining the 4-amino-3-substituted-butanoic acid derivative with an amino acid as a stabilizer and, if necessary, an auxiliary agent necessary for manufacturing a pharmaceutical preparation.

And further, the invention relates to a process for the preparation of a stabilized pharmaceutical preparation containing a 4-amino-3-substituted-butanoic acid derivative which is in a solid or liquid form.

The pharmaceutical preparation containing a 4-amino-3-substituted-butanoic acid derivative stabilized by an amino acid according to the invention may be formulated into various dosage forms including liquid pharmaceutical preparations such as syrups or liquid preparations or solid pharmaceutical preparations such as powders, granules, capsules or tablets.

Although the mechanism of action to stabilize a 4-amino-3-substituted-butanoic acid derivative with an amino acid has not yet been elucidated completely, it may be inferred that the amino group of the neutral amino acid and the carboxyl group of the neutral amino acid would act as blocking groups on the carboxyl group of the 4-amino-3-substituted-butanoic acid derivative and the amino group of the 4-amino-3-substituted butanoic acid derivative, respectively, to prevent autocondensation between the carboxyl group and amino group in the molecule of the 4-amino-3-substituted-butanoic acid derivative, whereby stabilization of the 4-amino-3-substituted-butanoic acid derivative will be eventually accomplished. However, the mechanism of action as depicted above is based upon a mere inference and patentability of the present invention obviously should not be influenced by whether this inference may be right or wrong.

As discussed above, the assumed mechanism of action to stabilize a 4-amino-3-substituted-butanoic acid derivative with an amino acid is based upon the so-called "ion pair" theory that the carboxyl and amino groups commonly contained in an amino acid may form the corresponding ion pairs with the amino and carboxyl groups of the 4-amino-3-substituted-butanoic acid derivative, respectively. However, the present stabilization effect can not necessarily be accomplished by all sorts of amino acids.

More specifically, the aminocarboxylic acid having an amino group at any position other than the α-position thereof such as the β-position thereof, for example, β-alanine or, even of the α-amino acids, the amino acids having a pyrrolidine ring such as proline, hydroxyproline, etc. may show a weak stabilizing effect, while the γ-amino acids having an amino group at the γ-position thereof such as γ-aminobutyric acid show no stabilizing effect.

Accordingly, the amino acid which may be employed as an effective stabilizer in the present invention is restricted to the α-amino acid having one free carboxyl group and one free amino group at the opposition thereof. In other words, all α-amino acids that have the said chemical structure can be used as a stabilizer in the present invention. The α-amino acid in the present invention (also referred to as an α-monoamino-monocarboxylic acid) may be any of acidic α-amino acids, basic α-amino acids, neutral α-amino acids and adducts of acidic α-amino acids with basic α-amino acids.

Examples of the α-amino acid which may be employed in this invention are illustrated below, but it is to be noted that the present invention should not be limited thereto.

The neutral α-amino acids may include glycine, phenylglycine, hydroxyphenylglycine, dihydroxyphenylglycine, L-alanine, hydroxy-L-alanine, L-leucine, hydroxy-L-leucine, dihydroxy-L-leucine, L-norleucine, methylene-L-norleucine, L-ketonorleucine, L-isoleucine, hydroxy-L-isoleucine, dihydroxy-L-isoleucine, L-valine, hydroxy-L-valine, L-isovaline, L-norvaline, hydroxy-L-norvaline, hydroxy-L-ketonorvaline, L-methionine, L-homomethionine, L-ethionine, L-threonine, acetyl-L-threonine, L-tryptophan, hydroxy-L-tryptophan, methyl-L-tryptophan, L-tyrosine, hydroxy-L-tyrosine, methyl-L-tyrosine, bromo-L-tyrosine, dibromo-L-tyrosine, 3,5-diiodo-L-tyrosine, acetyl-L-tyrosine, chloro-L-tyrosine, L-m-tyrosine, L-levodopa, L-methyldopa, L-thyroxine, L-serine, acetyl-L-serine, L-homoserine, acetyl-L-homoserine, ethyl-L-homoserine, propyl-L-homoserine, butyl-L-homoserine, L-cystine, L-homocystine, methyl-L-cystein, allyl-L-cysteine, propyl-L-cysteine, L-phenylalanine, dihydro-L-phenylalanine, hydroxymethyl-L-phenylalanine, L-aminobutyric acid, L-aminoisobutyric acid, L-ketoaminobutyric acid, dichloro-L-aminobutyric acid, dihydroxy-L-aminobutyric acid, phenyl-L-aminobutyric acid, L-aminovaleric acid, L-aminohydroxyvaleric acid, dihydroxy-L-aminovaleric acid, L-aminoisovaleric acid, L-aminohexanoic acid, methyl-L-aminohexanoic acid, L-aminoheptanoic acid, L-aminooctanoic acid and citrulline and the D- and DL-forms thereof.

The acidic α-amino acids may include L-aspartic acid, L-glutamic acid, L-carbocysteine, L-aminoglutaric acid, L-aminosuccinic acid, L-aminoadipic acid, L-aminopimelic acid, hydroxy-L-aminopimelic acid, methyl-L-aspartic acid, hydroxy-L-aspartic acid, methyl-L-glutamic acid, methylhydroxy-L-glutamic acid, L-methyleneglutamic acid, hydroxy-L-glutamic acid, dihydroxy-L-glutamic acid, hydroxy-L-aminoadipic acid or the like and the D- and DL-forms thereof.

The basic α-amino acids may include L-arginine. L-lysine. L-ornithine, L-canavanine, L-canaline, hydroxy-L-lysine, L-homoarginine, hydroxy-L-homoarginine, hydroxy-L-omithine, L-diaminopropionic acid, L-diaminohexanoic acid, L-diaminobutyric acid. L-diaminovaleric acid, L-diaminoheptanoic acid, L-diaminooctanoic acid or the like and the D- and DL-forms thereof.

The α,ω-diaminodicarboxylic acid may include diaminosuccinic acid, diaminoglutaric acid, diaminoadipic acid, diaminopimelic acid or the like.

Where the acidic α-amino acid is used as a stabilizer for a 4-amino-3-substituted-butanoic acid derivative in this invention, the amino acid may be used in the form of an alkali salt thereof such as aspartic acid Na salt, aspartic acid K salt, glutamic acid Na salt, glutamic acid K salt, aminopimelic acid Na salt, aminopimelic acid K salt or the like; an acid amide thereof such as asparagine, hydroxyasparagine, glutamine, hydroxyglutamine, methyleneglutamine or the like; an alkyl-substituted derivative of said acid amide such as methylasparagine, methylglutamine, ethylasparagine, ethylglutamine, isopropylglutamine, hydroxyphenylasparagine, hydroxyphenylglutamine, hydroxyethylasparagine, hydroxyethylglutamine or the like; an alkyl ester thereof such as methyl, ethyl or propyl ester of aspartic acid, methyl, ethyl or propyl ester of glutamic acid or the like.

Where the basic α-amino acid is used as a stabilizer in the invention, the amino acid may be used in the form of an acid addition salt thereof such as arginine hydrochloride, arginine acetate, lysine hydrochloride, lysine acetate, ornithine acetate or the like or a monoacylated derivative thereof such as acetyllysine, acetylornithine, acetylamino-aminobutyric acid, acetylamino-aminopropionic acid or the like.

And further, the acidic α-amino acid and the basic α-amino acid may be used in the form of the corresponding acidic amino acid-basic amino acid adduct such as aspartic acid-arginine, aspartic acid-lysine, aspartic acid-ornithine, glutamic acid-arginine, glutamic acid-lysine, or glutamic acid-ornithine adduct or the like.

Any of the α-amino acid mentioned above may be used alone or in combination with two or more thereof for liquid or solid pharmaceutical preparations of a 4-amino-3-substituted-butanoic acid derivative.

In preparing the liquid pharmaceutical preparation, the amino acid stabilizer of the invention may be blended with a 4-amino-3-substituted-butanoic acid derivative and then the resulting mixture may be simply dissolved in water to accomplish the object of stabilizing the 4-amino-3-substituted-butanoic acid derivative; provided that the 4-amino-3-substituted-butanoic acid derivative to be used is limited solely to the monoamino-monocarboxylic acid.

In preparing the liquid pharmaceutical preparation for oral administration, there may be incorporated, if required, a sweetening agent and/or a flavoring agent, which do not influence on the effect of the amino acid stabilizer. Also, the amino acids may exert the effect as a stabilizer on injections or transfusions for which sterilization such as high pressure steam sterilization is required.

When a masking effect against a bitter taste peculiar to a 4-amino-3-substituted-butanoic acid derivative is rather expected in a liquid pharmaceutical preparation, in addition to the stabilizing effect, it is preferable to use glycine, L-alanine, D-alanine, DL-alanine, Na glutamate and Na aspartate alone or in any combination thereof, because these amino acids have a potent buffering action on the 4-amino-3-substituted-butanoic acid derivative.

On the other hand, there are various embodiments for adding the amino acid stabilizer to a 4-amino-3-substituted-butanoic acid derivative in a solid pharmaceutical preparation. These embodiments may generally be divided into two types, i.e., a wet admixture wherein a solution of the amino acid dissolved in a solvent such as water or the like is added to the 4-amino-3-substituted-butanoic acid derivative and a dry admixture wherein the amino acid in a dry state is added to the 4-amino-3-substituted-butanoic acid derivative.

The wet admixture of the amino acid may be carried out during the manufacture of a pharmaceutical preparation of a 4-amino-3-substituted-butanoic acid derivative, for example, in a wet granulation step wherein the amino acid in the form of its solution or suspension is added to bulk powders of the 4-amino-3-substituted-butanoic acid derivative together with a binder and an auxiliary agent for manufacturing a pharmaceutical preparation, or in a coating step to apply a coating to granules or tablets for the purpose of masking a bitter taste wherein the amino acid is dissolved or suspended in a coating film base.

The wet granulation step of a 4-amino-3-substituted-butanoic acid derivative may be carried out by adopting any granulation method well-known per se, for example, a fluidized granulation method, a high speed stirring granulation method, a melting granulation method or the like. There may be preferably employed a fluidized granulation method in which bulk powders of the 4-amino-3-substituted-butanoic acid derivative are fluidized and then a solution or suspension of a stabilizer and, if necessary, a binder and other auxiliary agents for manufacturing a pharmaceutical preparation may be sprayed on the fluidized powders.

In the granulation step, granulation may be carried out by adding to bulk powders of a 4-amino-3-substituted-butanoic acid derivative the stabilizer solution as described above and, if necessary, a binder such as corn starch, a cellulose derivative (e.g., hydroxypropyl-cellulose), polyvinyl alcohol, a polyvinyl pyrrolidone (e.g., Kollidon-K30 or Kollidon-K25), a copolyvidone (e.g., Kollidon-VA64) and the like in the form of a solution or suspension thereof. The stabilizer may be added to bulk powders of the 4-amino-3-substituted-butanoic acid derivative by a wet or dry admixture using a binder or other auxiliary agents for manufacturing a pharmaceutical preparation, and thereafter the granulation may be carried out. In this granulation step, there may be also incorporated, if necessary, a sweetening agent such as mannitol, xylitol, sorbitol, aspartame and the like.

In the wet coating step of granules or tablets, there may be used as a film-forming material a polymeric base in the form of a solution or suspension such as a cellulose derivative, e.g., hydroxypropylcellulose or hydroxypropylmethylcellulose, a polyvinyl pyrrolidone, a copolyvidone, Eudragits and the like and, if necessary, a sweetening agent such as mannitol, xylitol, sorbitol, aspartame or the like. In this step, when it is rather expected to achieve a masking effect against a bitter taste of gabapentin, apart from the stabilizing effect, it is preferred, as is in the case of a liquid pharmaceutical preparation, to use L-alanine, D-alanine, DL-alanine, sodium glutamate or sodium aspartate alone or in any combination thereof. Also, when a lubricant effect is expected, it is preferable to use L-leucine, L-isoleucine, L-valine, D-leucine, D-isoleucine, D-valine, DL-leucine, DL-isoleucine or DL-valine.

Surface-coating of granules or tablets may be carried out by a well-known method using a fluidized bed or a rotary pan.

The dry admixture of the amino acid may be carried out, beside the dry admixture in the aforementioned wet granulation step, in a mixing step of powders prepared, for example, for compression using a tablet machine, for filling into hard capsules using a capsule filling machine or for filling using a distribution machine or the like.

When a lubricant effect is expected in addition to the stabilizing effect in the above steps, it is preferable to use L-leucine, L-isoleucine. L-valine, D-leucine, D-isoleucine, D-valine, DL-leucine, DL-isoleucine or DL-valine.

And further, in the dry mixing step, the amino acid may be usually blended with, as required, an auxiliary agent for manufacturing a pharmaceutical preparation, for example, a binder or a disintegrator such as a cellulose derivative, e.g., hydroxypropylcellulose, crystalline cellulose, corn starch, partially gelatinized starch or lactose or the like and/or a sweetening agent such as mannitol, xylitol, sorbitol, aspartame or the like by means of a suitable mixer such as a well-known dry mixer, e.g., a V-blender or the like.

The solid pharmaceutical preparation of a 4-amino-3-substituted-butanoic acid derivative which has been stabilized by the addition of the amino acid can be formulated in the compressed dosage form of, for example, tablets or in the fluidized dosage form of, for example, granules, so that the resulting dosage form may be easily ingested when orally administered to human.

Also, when the solid pharmaceutical preparation is administered in the form of an aqueous solution or suspension thereof, for example, in the case of dry syrups or effervescent tablets as dissolved or suspended in water, a stabilizing effect may be accomplished as in the case of the liquid pharmaceutical preparation.

As explained above, the pharmaceutical preparation of a 4-amino-3-substituted-butanoic acid derivative of the invention includes both of liquid and solid pharmaceutical preparations and a total amount of the amino acid as a stabilizer in a liquid pharmaceutical preparation may be in the range of 0.005-80 moles, preferably 0.01-70 moles, per 1 mole of the 4-amino-3-substituted-butanoic acid derivative, and in a solid pharmaceutical preparation, it may be in the range of 0.001-80 moles. Although in the latter case, the amino acid may preferably be used in the amount as defined above, the amount may vary depending upon the dosage form, a sort of the auxiliary agent to be used as well as the amount thereof to be blended. The amino acid when used beyond the upper limit would not noticeably lower or vitiate its effect. Thus, for example, when the amino acid is to be blended as an auxiliary agent including trituraded powders for manufacturing a pharmaceutical preparation, the upper limit of the amount to be blended is not limited to the application range as defined above.

As stated above, a remarkable stabilization effect can be obtained in the present pharmaceutical preparation of a 4-amino-3-substituted-butanoic acid derivative by using the amino acid as a stabilizer. Moreover, in the case where the said preparation is in the form of a solid pharmaceutical preparation, there may be concomitantly used the humectant which is used as a stabilizer for the pharmaceutical preparation of a 4-amino-3-substituted-butanoic acid derivative as disclosed and claimed in our copending application filed on the same date, depending upon the dosage form and manufacturing steps for the preparation, whereupon the amino acid and humectant as used are not adversely prevented each other from exerting their effect as a stabilizer.

The invention will be more fully explained by way of the following examples, but it should not be construed that these examples are limiting the scope of the invention.

EXAMPLE 1

In this Example, the following Samples (a), (b) and (c) of aqueous solutions of gabapentin were tested for stability.

Preparation of Samples:

1) Sample (a) was prepared by dissolving 500 mg of gabapentin crystals in water to make up a total volume of 10 mL.

2) Sample (b) was prepared by dissolving 500 mg of gabapentin crystals and 329 mg of glycine in water to make up a total volume of 10 mL.

3) Sample (c) was prepared by dissolving 500 mg of gabapentin crystals and 513 mg of L-valine in water to make up a total volume of 10 mL.

Samples (a), (b) and (c) prepared as described above were stored under the conditions as defined in the following Table 3 and then a lactam content formed in each of the aqueous solutions was determined by means of HPLC.

The lactam content in this example and examples hereinafter is expressed in term of % by weight based on gabapentin.

TABLE 3

| Storage Conditions | Samples | | |
|---|---|---|---|
| | (a) | (b) | (c) |
| When initiated | 0.005 | 0.005 | 0.005 |
| 45° C./1 week (sealed) | 0.255 | 0.112 | 0.107 |
| 45° C./2 weeks (sealed) | 0.528 | 0.220 | 0.227 |
| 45° C./3 weeks (sealed) | 0.774 | 0.313 | 0.324 |
| 45° C./4 weeks (sealed) | 1.098 | 0.452 | 0.441 |

The above table shows that gabapentin in its aqueous solution could be prevented from the degradation with lapse of time (the lactam formation) by the addition of glycine or L-valine.

EXAMPLE 2

In this Example, the following Samples (d), (e) and (f) of aqueous solutions of gabapentin were tested for stability.

Preparation of Samples:

1) Sample (d) was prepared by dissolving 500 mg of gabapentin crystals in water to make up a total volume of 10 mL.

2) Sample (e) was prepared by dissolving 500 mg of gabapentin crystals and 1.5 g of xylitol in water to make up a total volume of 10 mL.

3) Sample (f) was prepared by dissolving 500 mg of gabapentin crystals, 219 mg of glycine and 1.5 g of xylitol in water to make up a total volume of 10 mL.

Samples (d), (e) and (f) prepared as described above were stored under the conditions as defined in the following Table 4 and then a lactam content formed in each of the aqueous solutions was determined by means of HPLC.

TABLE 4

| Storage Conditions | Samples | | |
|---|---|---|---|
| | (d) | (e) | (f) |
| When initiated | 0.008 | 0.008 | 0.008 |
| 45° C./1 week (sealed) | 0.253 | 0.311 | 0.178 |
| 45° C./2 weeks (sealed) | 0.543 | 0.616 | 0.375 |
| 45° C./3 weeks (sealed) | 0.846 | 0.947 | 0.570 |

The above table shows that gabapentin in its aqueous solution could be similarly prevented from the degradation with lapse of time (the lactam formation) by the addition of glycine even in the presence of xylitol.

EXAMPLE 3

In this Example, the following Samples (g) and (h) of aqueous solutions of gabapentin were tested for stability.

Preparation of Samples:

1) Sample (g) was prepared by dissolving 10 g of gabapentin crystals in water to make up a total volume of 200 mL.

2) Sample (h) was prepared by dissolving 25 g of gabapentin crystals, 8.25 g of glycine, 9.75 g of DL-alanine, 100 g of xylitol and 0.05 g of perfume in water to make up a total volume of 500 mL.

Samples (g) and (h) prepared as described above were stored under the conditions as defined in the following Table 5 and then a lactam content formed in each of the aqueous solutions was determined by means of HPLC.

TABLE 5

| Storage Conditions | Samples | |
|---|---|---|
| | (g) | (h) |
| When initiated | 0.005 | 0.004 |
| 40° C./2 weeks (sealed) | 0.347 | 0.147 |
| 40° C./4 weeks (sealed) | 0.621 | 0.303 |
| 40° C./6 weeks (sealed) | 0.922 | 0.449 |
| 30° C./2 months (sealed) | 0.384 | 0.159 |
| 30° C./4 months (sealed) | 0.665 | 0.325 |
| 30° C./6 months (sealed) | 0.973 | 0.441 |
| 25° C./6 months (sealed) | 0.341 | 0.163 |
| 25° C./12 months (sealed) | 0.702 | 0.310 |
| 15° C./6 months (sealed) | 0.094 | 0.039 |
| 15° C./12 months (sealed) | 0.180 | 0.073 |
| 5° C./6 months (sealed) | 0.018 | 0.009 |
| 5° C./12 months (sealed) | 0.033 | 0.014 |

The above table shows that gabapentin in its aqueous solution could be similarly prevented from the degradation with lapse of time (the lactam formation) at all test temperatures by the addition of glycine and DL-alanine in the presence of xylitol and perfume.

EXAMPLE 4

This Example will illustrate the preparation of a stabilized solid pharmaceutical preparation of gabapentin by the addition of the present stabilizer to gabapentin according to the wet admixture.

Preparation of Samples:

In this Example, Samples (i) and (j) of gabapentin granules were prepared as follows:

1) Using a fluidized bed granulation apparatus, 72 g of water was sprayed onto 250 g of gabapentin crystals and successively a solution prepared by dissolving 5 g of hydroxypropylcellulose in 58 g of water was sprayed thereon and the product was dried to form Sample (i) of gabapentin granules.

2) Using a fluidized bed granulation apparatus, a solution prepared by dissolving 10 g of glycine in 62 g of water was sprayed onto 250 g of gabapentin crystals and successively a solution prepared by dissolving 5 g of hydroxypropylcellulose in 58 g of water was sprayed thereon and the product was dried to form Sample (j) of gabapentin granules.

Samples (i) and (j) prepared as described above were stored under the conditions as defined in the following Table 6 and then a lactam content formed in each sample was determined by means of HPLC.

TABLE 6

| Storage Conditions | Samples | |
|---|---|---|
| | (i) | (j) |
| When initiated | 0.004 | 0.004 |
| 60° C./1 week (sealed) | 0.131 | 0.079 |
| 60° C./2 weeks (sealed) | 0.214 | 0.134 |

The above table shows that the degradation with lapse of time (the lactam formation) due to the presence of water and the binder hydroxy propylcellulose could be prevented by the presence of glycine.

EXAMPLE 5

This Example will illustrate the preparation of a stabilized solid pharmaceutical preparation of gabapentin by the addition of the amino acid to gabapentin according to the dry admixture.

Preparation of Samples:

In this Example, Sample (k) of gabapentin granules and Samples (l), (m) and (n) of gabapentin tablets were prepared as follows:

1) Using a fluidized bed granulation apparatus, a solution prepared by dissolving 5 g of copolyvidone (Kollidon-VA64) and 5 g of propylene glycol in 90 g of water was sprayed onto 250 g of gabapentin crystals, which was then dried to form Sample (k) of gabapentin granules.

2) Using a rotary tablet machine, the gabapentin granules prepared as described above were compressed to form tablets, each having a weight of 208 mg, a diameter of 8 mm, a thickness of 4.3 mm and a hardness of 2-3 kg, which were used as Sample (l).

3) The gabapentin granules prepared as described in the above 1) were admixed with magnesium stearate at 0.4% by weight relative to the granules and then compressed using a rotary tablet machine to form tablets, each having a weight of 208 mg, a diameter of 8 mm, a thickness of 4.3 mm and a hardness of 4-5 kg, which were used as Sample (m).

4) The gabapentin granules prepared as described in the above 1) were admixed with L-isoleucine at 2% by weight relative to the granules and then compressed using a rotary tablet machine to form tablets, each having a weight of 208 mg, a diameter of 8 mm, a thickness of 4.3 mm and a hardness of 4-5 kg, which were used as Sample (n).

Samples (k)-(n) prepared as described above were stored under the conditions as defined in the following Table 7 and then a lactam content formed in each sample was determined by means of HPLC.

TABLE 7

| Storage Conditions | Samples | | | |
|---|---|---|---|---|
| | (k) | (l) | (m) | (n) |
| When initiated | 0.005 | 0.005 | 0.005 | 0.005 |
| 60° C./1 week (sealed) | 0.031 | 0.085 | 0.236 | 0.083 |
| 60° C./2 weeks (sealed) | 0.048 | 0.145 | 0.449 | 0.157 |

It can be seen from comparison between the data of Samples (k) and (l) that the degradation with lapse of time (the lactam formation) of gabapentin could be accelerated by the compactness given by compressing wet granulates of gabapentin, while comparison between the data of Samples (m) and (n) reveals that the anticipated degradation with lapse of time (the lactam formation) of gabapentin by compacting the wet granulates could be prevented by using as a lubricant essential for compressing gabapentin L-isoleucine having a lubricant effect, instead of magnesium stearate.

EXAMPLE 6

This Example will illustrate the preparation of a stabilized solid pharmaceutical preparation of gabapentin by the addition of the amino acid to gabapentin according to the dry admixture.

Preparation of Samples:

In this Example, Samples (o), (p) and (q) of gabapentin tablets were prepared as follows:

1) Using a fluidized bed granulation apparatus, a solution prepared by dissolving 5 g of lactose in 91 g of water was sprayed onto 250 g of gabapentin crystals, which was then dried to form gabapentin granules.

2) Using a rotary tablet machine, the gabapentin granules prepared as described in the above 1) were admixed with magnesium stearate at 0.4% by weight relative to the gabapentin granules and then compressed to form tablets, each having a weight of 208 mg, a diameter of 8 mm, a thickness of 4.3 mm and a hardness of 3-4 kg, which were used as Sample (o).

3) The gabapentin granules prepared as described in the above 1) were admixed with calcium stearate at 0.2% by weight relative to the granules and then compressed using a rotary tablet machine to form tablets, each having a weight of 208 mg, a diameter of 8 mm, a thickness of 4.3 mm and a hardness of 3-4 kg, which were used as Sample (p).

4) The gabapentin granules prepared as described in the above 1) were admixed with L-isoleucine at 2% by weight relative to the granules and then compressed using a rotary tablet machine to form tablets, each having a weight of 212 mg, a diameter of 8 mm, a thickness of 4.3 mm and a hardness of 3-4 kg, which were used as Sample (q).

Samples (o)-(q) prepared as described above were stored under the conditions as defined in the following Table 8 and then a lactam content formed in each of the samples was determined by means of HPLC.

TABLE 8

| Storage Conditions | Samples | | |
|---|---|---|---|
| | (o) | (p) | (q) |
| When initiated | 0.005 | 0.005 | 0.005 |
| 60° C./1 week (sealed) | 0.236 | 0.118 | 0.068 |
| 60° C./2 weeks (sealed) | 15.625 | 0.267 | 0.150 |
| 50° C./85% humidity/2 weeks (sealed) | 0.187 | 0.090 | 0.082 |
| 50° C./85% humidity/4 weeks (sealed) | 10.259 | 0.440 | 0.378 |

It can be seen from the table that the anticipated degradation with lapse of time (the lactam formation) of gabapentin by compacting the wet granulates could be prevented by using as a lubricant essential for compressing gabapentin L-isoleucine having a lubricant effect, instead of magnesium stearate or calcium stearate.

EXAMPLE 7

This Example will illustrate that gabapentin could be stabilized by the addition of the amino acid according to the dry admixture.

Preparation of Samples:
1) From 600 mg of gabapentin crystals was prepared by means of a mortar a powdery sample in a compacted state as Sample (r).
2) From 600 mg of gabapentin crystals together with 180 mg of glycine was prepared by means of a mortar a powdery sample in a compacted state as Sample (s).

Samples (r) and (s) prepared as described above were stored under the conditions as defined in the following Table 9 and then a lactam content formed in each of the samples was determined by means of HPLC.

TABLE 9

| Storage Conditions | Samples | |
|---|---|---|
| | (r) | (s) |
| When initiated | 0.008 | 0.008 |
| 60° C./2 weeks (sealed) | 0.136 | 0.130 |
| 60° C./3 months (sealed) | 14.326 | 0.926 |
| 50° C./85% humidity/2 weeks (open) | 0.012 | 0.013 |
| 50° C./85% humidity/3 months (open) | 0.013 | 0.016 |

It can be seen from the above table that the anticipated degradation with lapse of time (the lactam, formation) of gabapentin in a compacted state could be prevented by the addition of the amino acid according to the dry admixture.

EXAMPLE 8

In this Example, the following samples (t), (u) and (v) were tested for stability in aqueous solutions of pregabalin.

Preparation of Samples:
1) Sample (t) was prepared by dissolving 1 g of pregabalin crystals in water to make up a total volume of 50 mL.
2) Sample (u) was prepared by dissolving 1 g of pregabalin crystals and 0.94 g of glycine in water to make up a total volume of 50 mL.
3) Sample (v) was prepared by dissolving 1 g of pregabalin crystals and 1.47 g of L-valine in water to make up a total volume of 50 mL.

Samples (t), (u) and (v) prepared as described above were stored under the conditions as defined in the following Table 10 and then a content of the dehydrated condensate formed in each of the aqueous solutions was determined by means of HPLC. In this Example and the following Examples, a content of the dehydrated condensate formed is expressed in terms of % by weight, based on pregabalin.

TABLE 10

| Storage Conditions | Samples | | |
|---|---|---|---|
| | (t) | (u) | (v) |
| When initiated | <0.001 | <0.001 | <0.001 |
| 45° C./1 week (sealed) | 0.049 | 0.024 | 0.024 |
| 45° C./4 weeks (sealed) | 0.098 | 0.051 | 0.050 |
| 45° C./6 weeks (sealed) | 0.159 | 0.079 | 0.077 |

The above table shows that pregabalin in its aqueous solution could be prevented from the degradation with lapse of time (the condensation with dehydration) by the addition of glycine or L-valine.

EXAMPLE 9

This Example will illustrate the preparation of a stabilized solid pharmaceutical preparation of pregabalin by the addition of the amino acid to pregabalin according to the dry admixture.

Preparation of Samples:
In this Example, Sample (aa) of pregabalin granules and Samples (ab), (ac) and (ad) of pregabalin tablets were prepared as follows:

Preparation of Samples:
1) 1 g of pregabalin crystals was prepared to powdery Sample (aa) in a compacted state by means of a mortar.
2) 1 g of pregabalin crystals was blended with 10 mg of magnesium stearate by means of a mortar to prepare mixed powdery Sample (ab) in a compacted state.
3) 1 g of pregabalin crystals was blended with 30 mg of talc by means of a mortar to prepare mixed powdery Sample (ac) in a compacted state.
4) 1 g of pregabalin crystals was blended with 30 mg of L-leucine by means of a mortar to prepare mixed powdery Sample (ad) in a compacted state.

Samples (aa), (ab), (ac) and (ad) prepared as described above and untreated pregabalin crystals were stored under the conditions as defined in the following Table 11 and then a content of the dehydrated condensate formed in each of the samples was determined by means of HPLC.

TABLE 11

| Storage Conditions | Untreated Pregabalin | Samples | | | |
|---|---|---|---|---|---|
| | | (aa) | (ab) | (ac) | (ad) |
| When initiated | <0.001 | <0.001 | <0.001 | <0.001 | <0.001 |
| 80° C./1 week (sealed) | 0.006 | 0.030 | 0.092 | 0.035 | 0.022 |
| 60° C./2 weeks (sealed) | 0.001 | 0.041 | 0.056 | 0.051 | 0.033 |

The above table shows that pregabalin could be prevented from the degradation with lapse of time (the condensation with dehydration) by the use of an amino acid as a lubricant which is considered as an essential material for manufacturing a solid pharmaceutical preparation.

EXAMPLE 10

In this Example, the following Samples (ae) and (af) were tested for stability in aqueous solutions of baclofen.

Preparation of Samples:

1) Sample (ae) was prepared by dissolving 0.05 g of baclofen crystals in water to make up a total volume of 50 mL.

2) Sample (af) was prepared by dissolving 0.05 g of baclofen crystals and 0.05 g of glycine in water to make up a total volume of 50 mL.

Samples (ae) and (af) prepared as described above were stored under the conditions as defined in the following Table 12 and then a content of the dehydrated condensate formed in each of the aqueous solutions was determined by means of HPLC.

In this Example and the following Example, a content of the dehydrated condensate thus formed is expressed in terms of % by weight, based on baclofen.

TABLE 12

| | Samples | |
|---|---|---|
| Storage Conditions | (ae) | (af) |
| When initiated | 0.10 | 0.10 |
| 60° C./1 week (sealed) | 0.53 | 0.28 |
| 60° C./2 weeks (sealed) | 0.92 | 0.54 |
| 60° C./3 weeks (sealed) | 1.33 | 0.80 |
| 45° C./2 weeks (sealed) | 0.33 | 0.21 |
| 45° C./8 weeks (sealed) | 0.62 | 0.29 |
| 121° C./15 minutes (high pressure steam sterilization) | 0.31 | 0.21 |

The above table shows that baclofen could be prevented from the degradation with lapse of time (the condensation with dehydration) in its aqueous solution by the addition of glycine under all the storage and heating conditions.

EXAMPLE 11

In this Example, the stabilization of baclofen according to the wet admixture with the amino acid was tested for the following Samples (ag) and (ah) of baclofen.

Preparation of Samples:

1) Sample (ag) was prepared by wetting 200 mg of baclofen crystals with 0.1 mL of water, forming granular powders by means of a mortar and then drying.

2) Sample (ah) was prepared by wetting 200 mg of baclofen crystals with 0.1 mL of a 2% aqueous solution of L-isoleucine, forming granular powders by means of a mortar and then drying.

Samples (ag) and (ah) prepared as described above and untreated baclofen crystals were stored under the conditions as defined in the following Table 13 and then a content of the dehydrated condensate formed in each of the samples was determined by means of HPLC.

TABLE 13

| | Untreated | Samples | |
|---|---|---|---|
| Storage Conditions | Baclofen | (ag) | (ah) |
| When initiated | 0.10 | 0.08 | 0.07 |
| 60° C./1 week (sealed) | 0.36 | 0.67 | 0.28 |
| 60° C./2 weeks (sealed) | 0.57 | 1.05 | 0.30 |
| 60° C./3 weeks (sealed) | 0.70 | 1.33 | 0.32 |

The above table shows that the degradation of baclofen with lapse of time (the condensation with dehydration) could be accelerated by the granulation using water and could be prevented by wet admixture of L-leucine.

According to the present invention, the stabilization of a pharmaceutical preparation containing a 4-amino-3-substituted-butanoic acid derivative can be accomplished by the addition of an amino acid. Moreover, the stabilization by the addition of an amino acid can be accomplished not only in solid pharmaceutical preparations but also in liquid pharmaceutical preparations, stabilization of which has not been succeeded. Thus, the present invention can provide diverse means to administer a pharmaceutical preparation of a 4-amino-3-substituted-butanoic acid derivative; for example, the difficulty encountered in the prior art when administered to children may be avoided by forming a pharmaceutical preparation of gabapentin in the dosage form of a liquid pharmaceutical preparation, and others. The present invention can be expected to greatly contribute to the development of a stabilized pharmaceutical preparation of a 4-amino-3-substituted-butanoic acid derivative.

What is claimed is:

1. A solid pharmaceutical composition comprising: (a) a neutral α amino acid, (b) a compound selected from the group consisting of gabapentin and pregabalin, and (c) optionally, one or more auxiliary agents, wherein the neutral α-amino acid is one or more selected from the group consisting of: glycine, phenylglycine, hydroxyphenylglycine, dihydroxyphenylglycine, L-alanine, hydroxy-L-alanine, L-leucine, hydroxy-L-leucine, dihydroxy-L-Leucine, L-norleucine, methylene-L-norleucine, L-ketonorleucine, L-isoleucine, hydroxy-L-isoleucine, dihydroxy-L-isoleucine, L-valine, hydroxy-L-valine, L-isovaline, L-norvaline, hydroxy-L-norvaline, hydroxy-L-ketonorvaline, L-methionine, L-homomethionine, L-ethionine, L-threonine, acetyl-L-threonine, L-tryptophan, hydroxy-L-tryptophan, methyl-L-tryptophan, L-tyrosine, hydroxy-L-tyrosine, methyl-L-tyrosine, bromo-L-tyrosine, dibromo-L-tyrosine, 3,5-diiodo-L-tyrosine, acetyl-L-tyrosine, chloro-L-tyrosine, L-m-tyrosine, L-levodopa, L-methyldopa, L-thyroxine, L-serine, acetyl-L-serine, L-homoserine, acetyl-L-homoserine, ethyl-L-homoserine, propyl-L-homoserine, butyl-L-homoserine, L-cystine, L-homocystine, methyl-L-cysteine, allyl-L-cysteine, propyl-L-cysteine, L-phenylalanine, dihydro-L-phenylalanine, hydroxymethyl-L-phenylalanine, L-aminobutyric acid, L-aminoisobutyric acid, L-ketoaminobutyric acid, dichloro-L-aminobutyric acid, dihydroxy-L-aminobutyric acid, phenyl-L-aminobutyric acid, L-aminovaleric acid, L-aminohydroxyvaleric acid, dihydroxy-L-aminovaleric acid, L-aminoisovaleric acid, L-aminohexanoic acid, methyl-L-aminohexanoic acid, L-aminoheptanoic acid, L-aminooctanoic acid, citrulline, and the D- or DL-forms thereof.

2. The composition of claim 1, wherein the neutral α-amino acid is one or more selected from the group consisting:

glycine, phenylglycine, hydroxyphenylglycine, dihydroxyphenylglycine, L-alanine, hydroxy-L-alanine, L-leucine, hydroxy-L-leucine, dihydroxy-L-leucine, L-isoleucine, hydroxy-L-isoleucine, dihydroxy-L-isoleucine, L-valine, hydroxy-L-valine, L-isovaline, or D- and DL- forms thereof.

3. The composition of claim 1, wherein a total amount of the neutral α-amino acid is in the range of 0.001-80 moles per mole of the compound.

4. The composition of claim 1, wherein the compound is gabapentin.

5. The composition of claim 1, wherein the compound is pregabalin.

* * * * *